United States Patent
Schneider et al.

(10) Patent No.: US 9,096,841 B2
(45) Date of Patent: Aug. 4, 2015

(54) PREPARATION OF BETA-AMINO ACIDS

(75) Inventors: Nina Schneider, Offenburg (DE);
Bernhard Hauer, Fussgönheim (DE);
Klaus Ditrich, Gönnheim (DE); Maeve O'Neil, Linarady (IE); Nick Turner,
Manchester (GB)

(73) Assignee: BASF SE, Ludwigshafen (DE)

( * ) Notice: Subject to any disclaimer, the term of this patent is extended or adjusted under 35 U.S.C. 154(b) by 4 days.

(21) Appl. No.: 13/496,086

(22) PCT Filed: Sep. 15, 2010

(86) PCT No.: PCT/EP2010/063558
§ 371 (c)(1),
(2), (4) Date: Jul. 9, 2012

(87) PCT Pub. No.: WO2011/032990
PCT Pub. Date: Mar. 24, 2011

(65) Prior Publication Data
US 2012/0270280 A1    Oct. 25, 2012

Related U.S. Application Data

(60) Provisional application No. 61/245,303, filed on Sep. 24, 2009.

(30) Foreign Application Priority Data

Sep. 15, 2009  (EP) .................................... 09170364

(51) Int. Cl.
C12P 13/04    (2006.01)
C12N 9/86    (2006.01)

(52) U.S. Cl.
CPC .. *C12N 9/86* (2013.01); *C12P 13/04* (2013.01)

(58) Field of Classification Search
CPC .............. C12P 13/04; C12N 9/86; C12N 9/78
USPC ................................................ 435/106, 231
See application file for complete search history.

(56) References Cited

U.S. PATENT DOCUMENTS

| | | |
|---|---|---|
| 6,596,520 B1 | 7/2003 | Friedrich et al. |
| 2010/0240928 A1 | 9/2010 | Kutzki et al. |
| 2010/0291640 A1 | 11/2010 | Stuermer et al. |
| 2010/0304448 A1 | 12/2010 | Sturmer et al. |
| 2010/0311037 A1 | 12/2010 | Hauer et al. |
| 2011/0137002 A1 | 6/2011 | Hauer et al. |
| 2011/0250655 A1 | 10/2011 | Schneider et al. |
| 2011/0275855 A1 | 11/2011 | Ditrich et al. |
| 2012/0070867 A1 | 3/2012 | Maurer et al. |
| 2012/0123155 A1 | 5/2012 | Hauer et al. |
| 2012/0135477 A1 | 5/2012 | Breuer et al. |

FOREIGN PATENT DOCUMENTS

| | | |
|---|---|---|
| DE | 100193773 | 10/2001 |
| EP | 1 069 183 A2 | 1/2001 |
| EP | 1149849 A1 | 10/2001 |
| JP | 6261787 A | 9/1994 |

OTHER PUBLICATIONS

U.S. Appl. No. 13/063,630.
Arcuri, et al., "On the mechanism of hydrolysis of hydantoins by D-hydantoinase from *Vigna angularis*: inhibition studies" Journal of Molecular Catalysis B: Enzymatic 21 (2003) pp. 107-111.
Arcuri, et al., "Resolution of DL-hydantoins by D-hydantoinase from *Vigna angularis*: Production of highly enantioenriched N-carbamoyl-D-phenylglycine at 100% conversion" Amino Acids (2000) 19: pp. 477-482.
Arcuri, et al., "Stability of immobilized D-hydantoinase from *Vigna angularis* and repeated cycles of highly enantioenriched production of N-carbamoyl-D-phenylglycines" Amino Acids (2004) 27: pp. 69-74.
Bretschneider, Chemie Ingenieur Technik 2009, 81, No. 8, p. 1255.
Bretschneider, et al. Chemie Ingenieur Technik 2010, 82, No. 1-2, pp. 161-165.
Database EMBL Database accession No. CV538774.
Database Uniprot Database accession No. A4ZOY7.
Database Uniprot Database accession No. B9SXX3.
Database Uniprot Database accession No. C6TEN9.
Dürr et al., "Distribution of hydantoinase activity in bacterial isolates from geographically distinct environmental sources", *Journal of Molecular Catalysis*, vol. 39, pp. 160-165 (2006).
Eadie et al., "The Partial Purification and Properties of Animal and Plant Hydantoinases", www.jbc.org, pp. 449-458(1949).
Fan et al., "Purification of D-hydantoinase from adzuki bean and its immobilization for N-carbamoyl-D-phenylglycine production", *Biochemical Engineering Journal*, vol. 8, pp. 157-164 (2001).
Gaebler et al., "On the Metabolism of Hydantoins and Hydantonic Acids", pp. 763-777 (1926).
Hamajima et al., "A novel gene family defined by human dihydropyrimidinase and three related proteins with differential tissue distribution", *Gene*, vol. 180 pp. 157-163 (1996).
May, et al., "Substrate-dependent enantioselectivity of a novel hydantoinase from *Arthrobacter aurescens* DSM 3745: Purification and characterization as new member of cyclic amidases" Journal of Biotechnology 61 (1998) pp. 1-13.

(Continued)

*Primary Examiner* — Tekchand Saidha
*Assistant Examiner* — Md. Younus Meah
(74) *Attorney, Agent, or Firm* — Drinker Biddle & Reath LLP

(57) ABSTRACT

The present invention relates to a process for the biocatalytic, enantioselective production of a β-amino acid precursor from an optionally substituted dihydrouracil using a hydantoinase and/or a dihydropyrimidinase, a process for producing a β-amino acid from said precursor, a hydantoinase and its use in said process for the biocatalytic production of a β-amino acid precursor or a β-amino acid, and a method for obtaining said hydantoinase.

18 Claims, 7 Drawing Sheets

(56) References Cited

OTHER PUBLICATIONS

Morin, et al. "Use of D-hydantoinase extracted from legumes to produce N-carbamyl D-amino acids" Enzyme Microb. Technol., 1993 vol. 15, March, pp. 208-214.

Ogawa, et al., "Diversity and versatility of microbial hydantoin-transforming enzymes" Journal of Molecular Catalysis B: Enzymatic 2 (1997) pp. 163-176.

Syldatk, et al., "Microbial hydantoinases—industrial enzymes from the origin of life" Appl Microbiol Biotechnol (1999) 51: pp. 293-309.

International Search Report for PCT/EP2010/063558.

Written Opinion of the International Searching Authority.

SEQUENCE LISTING

```
<160> NUMBER OF SEQ ID NOS: 7

<210> SEQ ID NO 1
<211> LENGTH: 19
<212> TYPE: PRT
<213> ORGANISM: Vigna angularis

<400> SEQUENCE: 1

Ile Glu Leu Gly Ile Thr Gly Pro Glu Gly Gln Arg Leu Ala Gly Pro
1               5                   10                  15

Thr Val Leu

<210> SEQ ID NO 2
<211> LENGTH: 18
<212> TYPE: PRT
<213> ORGANISM: Vigna angularis

<400> SEQUENCE: 2

Ile Glu Leu Gly Ile Thr Gly Pro Glu Gly Gln Arg Leu Ala Gly Pro
1               5                   10                  15

Val Leu

<210> SEQ ID NO 3
<211> LENGTH: 18
<212> TYPE: PRT
<213> ORGANISM: Vigna angularis
```

<400> SEQUENCE: 3

Ile Glu Leu Ile Thr Gly Pro Glu Gly Gln Arg Leu Ala Gly Pro Thr
1               5                   10                  15

Val Leu

<210> SEQ ID NO 4
<211> LENGTH: 17
<212> TYPE: PRT
<213> ORGANISM: Vigna angularis

<400> SEQUENCE: 4

Ile Glu Leu Ile Thr Gly Pro Glu Gly Gln Arg Leu Ala Gly Pro Val
1               5                   10                  15

Leu

<210> SEQ ID NO 5
<211> LENGTH: 20
<212> TYPE: PRT
<213> ORGANISM: Vigna angularis

<400> SEQUENCE: 5

Glu Glu Ile Ala Arg Ala Arg Lys Ser Gly Gln Arg Val Ile Gly Glu
1               5                   10                  15

Pro Val Ala Ser
            20

<210> SEQ ID NO 6
<211> LENGTH: 525
<212> TYPE: PRT
<213> ORGANISM: Glycine max

<400> SEQUENCE: 6

Met Gln Phe Ser Ile Thr Ser Gln Phe Leu His Ile Phe Ser Leu Thr
1               5                   10                  15

Ile Phe Ile Ile Ile Thr Ser Ser Leu Ser Gln Ser Ser Gln Phe Cys
            20                  25                  30

Asp Ala Gly Thr Glu Ile Pro Ser Ser Lys Leu Leu Ile Lys Gly Gly
        35                  40                  45

Thr Val Val Asn Ala Gln His His Gln Ile Ala Asp Val Tyr Val Glu
    50                  55                  60

Asp Gly Ile Ile Val Ala Val Asn Pro Asn Ile Met Val Gly Asp Asp
65                  70                  75                  80

Val Thr Val Ile Asp Ala Thr Gly Lys Tyr Val Met Pro Gly Gly Ile
                85                  90                  95

Asp Pro His Thr His Leu Asp Met Asp Val Gly Phe Thr Ala Thr Val
            100                 105                 110

Asp Asp Phe Phe Ser Gly Gln Ala Ala Leu Ala Gly Gly Thr Thr
        115                 120                 125

Met His Ile Asp Phe Val Ile Pro Leu Asn Gly Ser Leu Thr Ala Gly
    130                 135                 140

Phe Glu Asp Tyr Glu Lys Lys Ala Lys Ser Cys Met Asp Tyr Gly
145                 150                 155                 160

Phe His Met Val Ile Thr Lys Trp Asp Glu Thr Val Ser Arg Glu Met
                165                 170                 175

```
Glu Leu Met Val Lys Glu Lys Gly Ile Asn Ser Phe Lys Phe Phe Met
            180                 185                 190
Ala Tyr Lys Gly Ile Leu Met Ile Asn Asp Glu Leu Leu Leu Glu Gly
            195                 200                 205
Phe Lys Lys Cys Lys Ser Leu Gly Ala Val Ala Met Val His Ala Glu
            210                 215                 220
Asn Gly Asp Ala Val Tyr Glu Gly Gln Arg Lys Met Ile Glu Leu Gly
225                 230                 235                 240
Ile Thr Gly Pro Glu Gly His Ala Leu Ser Arg Pro Ala Val Leu Glu
            245                 250                 255
Gly Glu Ala Thr Ala Arg Ala Ile Arg Leu Ala Asp Phe Val Asn Thr
            260                 265                 270
Pro Leu Tyr Val Val His Val Met Ser Ile Asp Ala Met Glu Glu Ile
            275                 280                 285
Ala Lys Ala Arg Lys Ala Gly Gln Arg Val Ile Gly Glu Pro Ile Ala
            290                 295                 300
Ser Gly Leu Ala Leu Asp Glu Ser Trp Leu Trp His Pro Asp Phe Glu
305                 310                 315                 320
Ile Ala Ala Lys Tyr Val Met Ser Pro Pro Ile Arg Lys Arg Gly His
            325                 330                 335
Asp Lys Ala Leu Gln Ala Ala Leu Ser Thr Gly Val Leu Gln Leu Val
            340                 345                 350
Gly Thr Asp His Cys Ala Phe Asn Ser Thr Gln Lys Ala Arg Gly Ile
            355                 360                 365
Asp Asp Phe Arg Lys Met Pro Asn Gly Val Asn Gly Ile Glu Glu Arg
            370                 375                 380
Met His Leu Val Trp Asp Ile Met Val Glu Ser Gly Gln Ile Ser Val
385                 390                 395                 400
Thr Asp Tyr Val Arg Ile Thr Ser Thr Glu Cys Ala Lys Ile Phe Asn
            405                 410                 415
Ile Tyr Pro Arg Lys Gly Ala Val Leu Pro Gly Ser Asp Ala Asp Ile
            420                 425                 430
Ile Ile Leu Asn Pro Asn Ser Ser Phe Glu Met Ser Ala Lys Ser His
            435                 440                 445
His Ser Arg Leu Asp Thr Asn Val Tyr Glu Gly Arg Arg Gly Lys Gly
            450                 455                 460
Lys Ile Glu Val Thr Ile Ala Gly Gly Arg Val Val Trp Glu Asn Asn
465                 470                 475                 480
Glu Leu Lys Val Thr Pro Gly Thr Gly Arg Tyr Ile Gln Met Pro Pro
            485                 490                 495
Phe Ser Tyr Leu Phe Asp Gly Leu Asp Lys Lys Asp Ala Ile Tyr Leu
            500                 505                 510
Asn Ser Leu Gln Ala Pro Val Lys Arg Ala Lys Ala Ser
            515                 520                 525

<210> SEQ ID NO 7
<211> LENGTH: 12
<212> TYPE: PRT
<213> ORGANISM: Vigna angularis

<400> SEQUENCE: 7

Ile Thr Gly Pro Glu Gly Gln Arg Leu Ala Gly Pro
1               5                   10
```

PREPARATION OF BETA-AMINO ACIDS

RELATED APPLICATIONS

This application is a national stage application (under 35 U.S.C. §371) of PCT/EP2010/063558, filed Sep. 15, 2010, which claims benefit of European Application No. 09170364.5, filed Sep. 15, 2010, and U.S. Provisional Patent Application Ser. No. 61/245,303, filed Sep. 24, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00230_U.S. The size of the text file is 7 KB and the text file was created on Mar. 14, 2012.

FIELD OF THE INVENTION

The present invention relates to a process for the biocatalytic production of a β-amino acid precursor from an optionally substituted dihydrouracil using a hydantoinase and/or a dihydropyrimidinase, a process for producing a β-amino acid from said precursor, a hydantoinase and its use in said process for the biocatalytic production of a β-amino acid precursor or a β-amino acid, and a method for obtaining said hydantoinase.

BACKGROUND ART

Enantiomerically pure β-amino acids are valuable building blocks for novel therapeutics agents that possess a wide range of biological activity. Although a number of biocatalytic routes have been developed for their preparation, no single method has emerged as being universally applicable. Similarly, few chemo-catalytic routes to β-amino acids have been developed, most requiring stoichiometric quantities of chiral auxiliaries.

Dihydropyrimidinases and hydantoinase are possible candidates for the biocatalytic synthesis of amino acids or their precursors. Gaebler and Keltch first reported hydantoinase cleaving activities in 1920s (Gaebler, O. H.; Keltch, A. K. *On the metabolism of hydantoins and hydantoic acid,* 1926; Vol. 70). It was initially suggested by Eadie et al. in the 1950s that microbial hydantoinases were identical to animal dihydropyrimidinase (Eadie, G.; Bernheim, F.; Bernheim, M. Journal of Biological Chemistry 181: 449-458, 1949). Dihydropyrimidinase enzymes, isolated from calf liver and plants, catalysed the hydrolysis of dihydrouracil and dihydrothymine into the N-carbamoyl-β-alanine and N-carbamoyl-2-methyl-β-alanine, respectively. These enzymes also cleaved (R)-5-monosubsitituted hydantoin into (R)—N-carbamoyl-amino acid. Recent literature generally proposes that D-hydantoinase from microbial sources can be considered to be the counterpart of animal dihydropyrimidinase, with Nonaka and co-workers, suggesting an evolutionary relationship between these two enzymes (Hamajima, N.; Matsuda, K.; Sakata, S.; Tamaki, N.; Sasaki, M.; Nonaka, M. Gene 180:157-163, 1996). Syldatk et al. conclude that dihydropyrimidinases and hydantoinases are not necessarily the same enzyme (Syldatk, C.; May, O.; Altenbuchner, J.; Mattes, R.; Siemann, M. Applied Microbiology and Biotechnology 51:293-309, 1999). The different entantioselecivities of hydantoinases are often used to group them, according to their specificity, as D-, L-, or nonspecific (Ogawa, J.; Shimizu, S. Journal of Molecular Catalysis B: Enzymatic 2:163-176, 1997).

Problems arising from the naming system used for the hydantoinase and dihydropyrimidinase enzymes are further aggravated by the fact that often, especially in earlier journals, the terms were used interchangeably. Amidohydrolases, also referred to as cyclic amidases [E.C.3.5.2], are a group of more than 14 enzymes all acting on cyclic amide rings and containing a number of highly conserved regions and invariant amino acid regions (Kim, G. J.; Cheon, Y. H.; Kim, H. S. *Biotechnology and Bioengineering* 1998, 61, 1-13). Comprised in this group are carboxylmethylhydantoinase [E.C.3.5.2.4], allantoinase [E.C.3.5.2.5], 1-methylhydantoinase [E.C.3.5.2.14] and carboxyethyl-hydantoinase, all of which are technically the only hydantoinases, as their substrates are naturally occurring hydantoin derivatives.

Other enzymes which fall into the wider grouping of cyclic amidases include dihydroorotase [E.C.3.5.2.3] and dihydropyrimidinase [E.C.3.5.2.2], the latter of which is commonly referred to as D-hydantoinase, due to its ability to hydrolyse (R)-5-monosubstituted hydantoin derivatives. This superfamily of proteins most likely evolved in prehistoric earth, when N-carbamoyl-amino acids are hypothesised to have been the original synthons of prebiotic peptides.

The use of hydantoinases for the enantioselective hydrolysis of racemic mixtures of 5-substituted hydantoins (R)-1 and (S)-1 to their corresponding N-carbamoyl derivatives (R)-2 and (S)-2 is well established (cf. Scheme 1 below) and described in literature (Morin, Enzyme Microb. Technol. 15:208-214, 1993; Fan and Lee, Biochemical Engineering J. 8:157-164, 2001; Arcuri et al., J. Molecular Catalysis B 21:107-111, 2003; Arcuri et al., Amino Acids 19:477-482, 2000). It has been developed to the stage where commercial processes now operate at scale for the production of specific D-(R)-amino acids (R)-3 using this technology. A key aspect of these processes is the in situ racemisation of the unreacted enantiomer (S)-1 together with carbamoylase catalysed hydrolysis of (R)-2 leading to a dynamic kinetic resolution (DKR) reaction.

Scheme 1

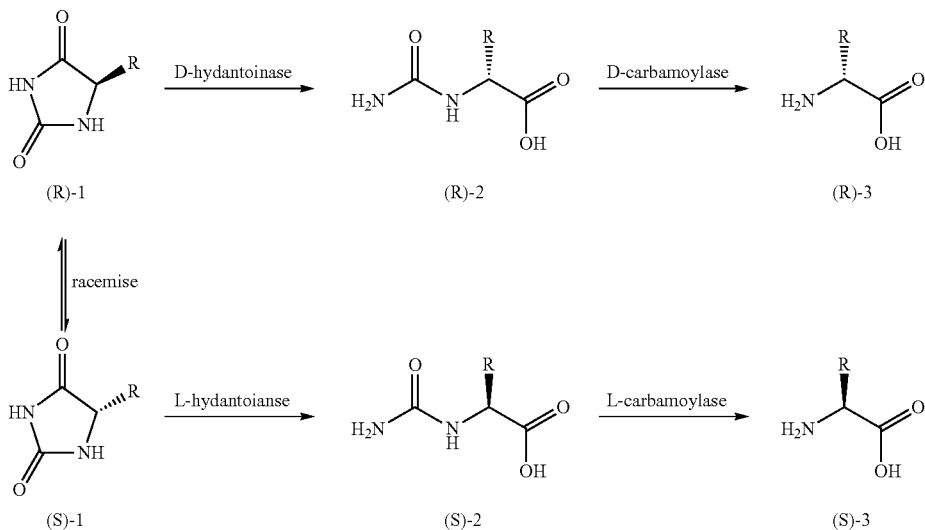

Kinetic resolution occurs when an enzyme turns over one enantiomer faster than the other. However, the maximum yield for this type of reaction is only 50%, and the products need to be separated from the starting material. In a dynamic kinetic resolution the enantiomers are racemized, so that (R)- and (S)-enantiomers form a chemical equilibrium and readily interconvert. When the faster reacting enantiomer is converted to the corresponding product, it is replenished due to the racemisation, thereby allowing yields of up to 100%.

In contrast to the enantioselective hydrolysis of racemic 5-substituted hydantoins, the possibility of carrying out enantioselective hydrolysis of 6-substituted dihydrouracils (+/−)-4 (cf. Scheme 2) to their corresponding N-carbamoyl derivatives (R or S)-5, as a route to β-amino acids (R or S)-6, has received very little attention. Syldatk et al., in 1998 (May, O.; Siemann, M.; Pietzsch, M.; Kiess, M.; Mattes, R.; Syldatk, C. J. Biotechnol. 61:1-13, 1998) reported the use of a hydantoinase from *Arthrobacter aurescens* for the hydrolysis of dihydrouracil ((+/−)-4, wherein R stands for H) and subsequently in 2003 described in a poster that this hydantoinase could be applied to the resolution of 6-phenyldihydrouracil (6-PDHU, (+/−)-4, wherein R stands for phenyl) although poor enantioselectivity and low reaction rates relative to 5-phenylhydantoin ((R)-1 and (S)-1, respectively, wherein R stands for Ph in Scheme 1) were observed.

Scheme 2

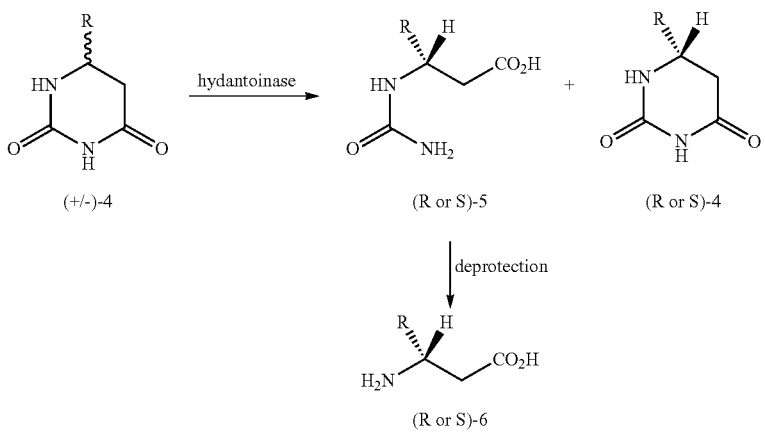

The Japanese patent application JP06261787 reported enantiomeric excess rates of up to 51% for the hydrolysis of 6-PDHU using *Pseudomonas putida* IFO 12996; better selectivities (up to 93% of enantiomeric excess) were obtained with substrates containing 6-alkyl substituents. Clearly, there is need for improved methods for the biocatalytic production of β-amino acid precursors or β-amino acids.

BRIEF DESCRIPTION OF THE INVENTION

In a first aspect the object of the present invention was solved by a process for the biocatalytic, stereospecific, in particular enantioselective, production of a β-amino acid precursor, comprising reacting at least one substrate of the general formula (I)

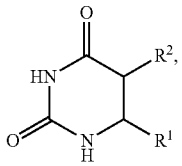

(I)

wherein $R^1$ and $R^2$ independently from each other are selected from hydrogen;
a linear or branched, optionally substituted, lower alkyl group;
a linear or branched, optionally substituted, lower alkenyl group;
an optionally substituted cyclic alkyl group;
a mono- or polycyclic, optionally substituted aryl group;
a mono- or polycyclic, optionally substituted heteroaryl group;
a linear or branched, optionally substituted alkoxy group;
an amino group;
a linear or branched, optionally substituted alkylamino group;
a linear or branched, optionally substituted alkylthio group;
a linear or branched, optionally substituted acyl group,
a carboxyl group or
an aldehyde group;
in stereoisomerically pure form, as for example (R)- or (S)-isomer, or as a mixture of stereoisomers, as for example as racemic mixture,
or a salt of said compound, as for example an acid addition salt
in the presence of at least one enzyme, catalyzing the hydrolytic cleavage of a hydantoin and/or dihydropyrimidin ring, in particular, selected among a hydantoinase and a dihydropyrimidinase, more particular being an hydantoinase, in particular an enzyme having preference for a particular stereoisomer of the compound to be converted; and optionally in the presence of at least one enzyme having the ability to interconvert the stereoisomers of said compound of formula (1),
so that a β-amino acid precursor of the general formula (II)

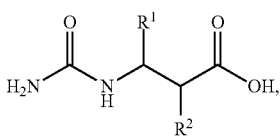

(II)

wherein $R^1$ and $R^2$ are identified as above,
is produced;
said process being characterized in that the at least one enzyme catalyzing the hydrolytic cleavage of a hydantoin and/or dihydropyrimidin ring, in particular a hydantoinase and/or dihydropyrimidinase, is obtained from *Vigna angularis* and/or comprises at least one partial sequence having an identity of about 60 to 100% to at least one of the following partial sequences:

| | |
|---|---|
| ITGPEGQRLAGP | (SEQ ID NO: 7) |
| IELGITGPEGQRLAGPTVL | (SEQ ID NO: 1) |
| IELGITGPEGQRLAGPVL | (SEQ ID NO: 2) |

-continued

| | |
|---|---|
| IELITGPEGQRLAGPTVL | (SEQ ID NO: 3) |
| IELITGPEGQRLAGPVL | (SEQ ID NO: 4) |
| EEIARARKSGQRVIGEPVAS, | (SEQ ID NO: 5) | as for example comprises at least one partial sequence having an identity of between 60% and 100% to at least one of the partial sequences SEQ ID NO: 5 and 7.

According to one embodiment the process furthermore comprises an additional step by converting said β-amino acid precursor of formula (2) to the corresponding β-amino acid of the formula (III)

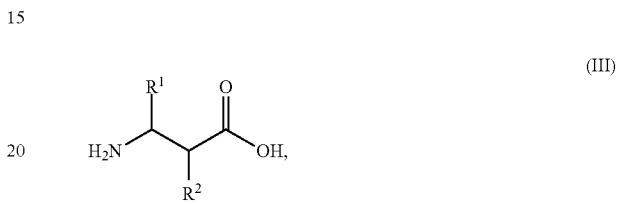

(III)

wherein $R^1$ and $R^2$ have the same meaning as previously defined.

According to a further embodiment, the conversion of the β-amino acid precursor takes place at an acidic pH, preferentially in the presence of nitrous acid, or in the presence of a carbamoylase.

According to a further embodiment, the at least one hydantoinase and/or dihydropyrimidinase (in particular enzymes according to E.C. 3.5.2.2) is an enzyme obtainable from an organism of the genus *Agrobacterium*, *Arthrobacter*, *Pseudomonas* and *Vigna*, in particular *Vigna angularis*.

According to a further embodiment, $R^2$ is H and $R^1$ different from H in the general formulae (I) to (III).

According to a further embodiment, $R^2$ is H and $R^1$ is an optionally substituted aryl group in the general formulae (I) to (III).

In particular, the compounds of formulae (II) and (III) and also of formula (I), wherein merely $R^2$ is H, and $R^1$ is different from H, preferably are present as (S)-isomer in stereoisomerically pure form or in stereoisomeric excess (in particular having an ee-value of more than 93%, preferentially in the range of 95-99%, or more than 99%).

According to a further embodiment, the reaction is performed in a Tris-buffered or a borate-buffered reaction mixture, preferentially a Tris-buffered reaction mixture.

According to a further embodiment, the reaction is performed at a pH from about 7.0 to about 11.0, preferentially at a pH from about 7.5 to about 10.0, and especially preferred at a pH from about 7.5 to about 8.0.

According to a further embodiment, the reaction is performed in the presence of approximately 1% to approximately 20% dimethylsulfoxide, preferentially in the presence of approximately 10% dimethylsulfoxide.

According to a further embodiment, the reaction is performed at a temperature in the range of about 30° C. to about 60° C., preferentially from about 30° C. to about 50° C., and in particular from about 40° C. to about 50° C.

According to a further embodiment, the reaction is performed from about 1 hour to about 25 hours, preferentially from about 3 hours to about 10 hours, an in particular about 4 hours to about 5 hours.

According to a further embodiment, the at least one substrate is selected among a dihydrouracil, which is monosubstituted at the 5-position or at the 6-position, in particular 6-phenyldihydrouracil, 6-(4-fluoro-phenyl)-dihydrouracil, 6-(4-chloro-phenyl)-dihydrouracil, 5-methyldihydrouracil and 6-methyldihydrouracil.

A further aspect of the present invention relates to the use of a β-amino acid precursor or a β-amino acid as obtainable by a process according to the invention for manufacturing hydrolytically stable peptides, pharmaceutically active agents, in particular antibiotic, anticancer, antithrombotic, antifungal insecticidal, anthelminthic, nonpeptide integrin antagonist, alkaloids and/or cytotoxic agents.

A further aspect of the present invention relates to the use of a hydantoinase and/or a dihydropyrimidinase comprising at least one partial sequence having an identity of between 60 percent and 100 percent to at least one of the following partial sequences:

| | |
|---|---|
| ITGPEGQRLAGP | (SEQ ID NO: 7) |
| IELGITGPEGQRLAGPTVL | (SEQ ID NO: 1) |
| IELGITGPEGQRLAGPVL | (SEQ ID NO: 2) |
| IELITGPEGQRLAGPTVL | (SEQ ID NO: 3) |
| IELITGPEGQRLAGPVL | (SEQ ID NO: 4) |
| EEIARARKSGQRVIGEPVAS, | (SEQ ID NO: 5) | as for example at least one of the partial sequences: SEQ ID NO: 5 and 7, for a process according to the invention.

A further aspect of the present invention relates to a substantially pure hydantoinase, containing at least one of the following partial sequences comprising at least one partial sequence having an identity of between 60 percent and 100 percent, for example 100 percent to at least one of the following partial sequences:

| | |
|---|---|
| ITGPEGQRLAGP | (SEQ ID NO: 7) |
| IELGITGPEGQRLAGPTVL | (SEQ ID NO: 1) |
| IELGITGPEGQRLAGPVL | (SEQ ID NO: 2) |
| IELITGPEGQRLAGPTVL | (SEQ ID NO: 3) |
| IELITGPEGQRLAGPVL | (SEQ ID NO: 4) |
| EEIARARKSGQRVIGEPVAS, | (SEQ ID NO: 5) | as for example at least one of the partial sequences: SEQ ID NO: 5 and 7.

A further aspect of the present invention relates to a substantially pure hydantoinase, obtained by preparing a crude extract of cell material from an organism naturally or recombinantly expressing said enzyme activity, and subjecting said crude extract to the sequential purification steps of
a) ion exchange chromatography
b) hydrophobic chromatography
c) gel filtration
d) affinity chromatography
e) anion exchange
f) gel filtration Further aspects of the present invention relate to substantially pure hydantoinase, which comprise at least one of SEQ ID NO:1 to 5 and 7 and/or are isolated according to the aforementioned method. Preferably, the hydantoinase is obtained from an organism of the genus *Agrobacterium*, *Arthrobacter*, *Pseudomonas* and *Vigna*, in particular *Vigna angularis*.

A further aspect relates to a hydantoinase, which comprises at least one of SEQ ID NO:1 to 5 and 7, is obtained from *Vigna angularis*, in particular by a method substantially comprising the above purification steps in any order is isolated according to the aforementioned method, and shows after SDS PAGE, in particular under reducing conditions, a protein band at 55±10, 55±5 or 55±2 or about 55 kD.

A further aspect of the invention relates to the use of an aforementioned hydantoinase for process for the biocatalytic production of a β-amino acid precursor or a β-amino acid according to the invention.

The aforementioned hydantoinase may in particular be a hydantoinase from an organism of the genus *Agrobacterium*, *Arthrobacter*, *Pseudomonas* and *Vigna*, in particular *Vigna angularis*.

A further aspect of the present invention relates to the use of any of the aforementioned hydantoinases for a method according to the invention.

DESCRIPTION OF THE FIGURES

In the following the present invention is described in a more detailed manner, wherein reference may be made to the figures.

DETAILED DESCRIPTION OF THE INVENTION

A. Definitions

Figure 1:
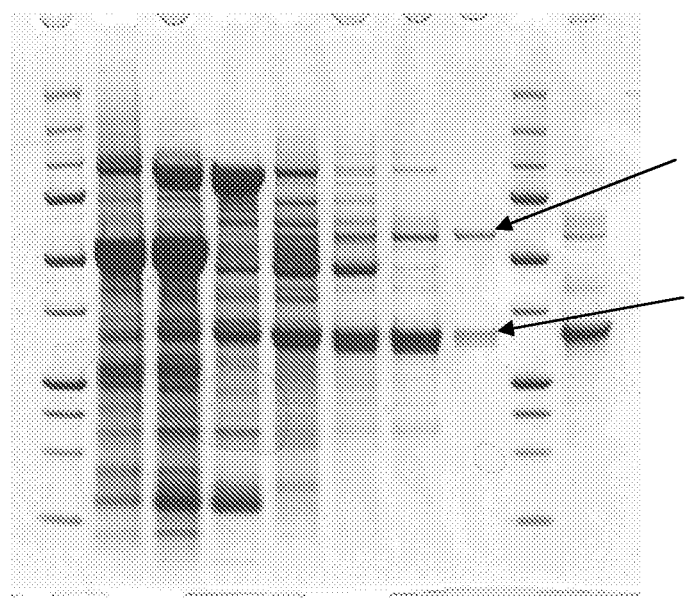
FIG. 1 shows an SDS PAGE gel of hydantoinase purified from *Vigna angularis*.

In the context of the invention "an enzyme catalyzing the hydrolytic cleavage of a hydantoin and/or dihydropyrimidin ring", like a substituted hydantoin and/or substituted dihydropyrimidin ring, as for example 5-phenylhydantoin and 6-phenyldihydrouracil, has to show the ability to catalyze the hydrolytic cleavage of at least one compound of formula (I) to form a compound of formula (II). In particular, such an enzyme may also be referred to as hydantoinase and/or dihydroyrimidinase, wherein an enzyme, whose natural substrate is a hydantoin ring, preferably would be referred to as a hydantoinase, and an enzyme, whose natural substrate is a dihydrouracil ring, preferably would be referred to as a dihydropyrimidinase.

In the context of the present invention, dihydropyrimidinases are characterized as enzymes which are capable of hydrolyzing dihydropyrimidines and, additionally, of hydrolyzing hydantoin (as shown in formula IV) and of resolving (±)-5-monosubstituted hydantoins as shown in Scheme 3.

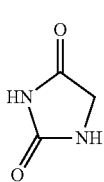

(IV)

Scheme 3

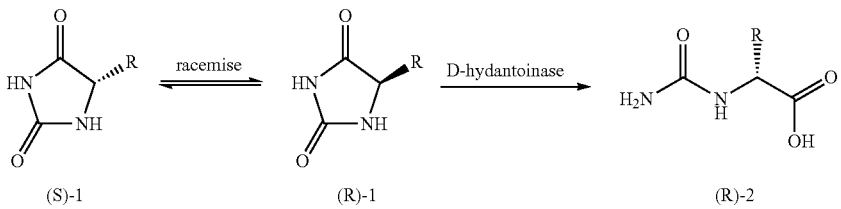

Conversely hydantoinases generally show little hydrolytic activity towards dihydropyrimidines, but can hydrolyse hydantoin and (±)-5-monosubstituted hydantoins. Suitable assays for hydrolysing hydantoin or dihydropyrimidine, and consequently for further defining enzymes applicable in the process of the invention, are for example described in Example 1.

The term "about" indicates a potential variation of ±25% of the stated value, in particular ±15%, ±10%, ±5% or ±4% or ±3% or ±2% or ±1%.

In the context of the present invention enantioselectivity means that the enantiomeric excess "ee" of the S-enantiomer, which is expressed in percent (%) and calculated on the basis of the respective concentrations of the S-enantiomer and the R-enantiomer as follows:

ee (%)=[(S-enantiomer−R-enantiomer)/(S-enantiomer+R-enantiomer)]×100, is at least 50%, preferentially at least 80%, more preferentially at least 90%, and in particular more than 93%, in particular at least 94%, at least 95%, at least 96%, at least 97%, at least 98%, at least 99%, or 100%.

As used herein, a "substantially pure" protein or enzyme means that the desired purified protein is essentially free (for example more than 90, 92, 93, 94, 95, 96, 97, 98, 99, or 99.9% (of dry weight) constitute said protein) from contaminating cellular components, as evidenced by a single band following polyacrylamide-sodium dodecyl sulfate gel electrophoresis (SDS-PAGE). The term "substantially pure" is further meant to describe a molecule, which is homogeneous by one or more purity or homogeneity characteristics used by those of skill in the art. For example, a substantially pure protein will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of said protein with other compounds. In addition, the term is not meant to exclude fusion proteins of said protein optionally isolated from a recombinant host.

B. Substrates for the Method According to the Invention

The residues $R^1$ and/or $R^2$ of a substrate according to the general formula (1) can be selected among linear or branched lower alkyl groups, which optionally may be substituted at one or more positions. The residues $R^1$ and $R^2$ can in particular be groups comprising straight chain or branched alkyl groups containing 1 to 10 carbon atoms, in particular 2 to 6 carbon atoms, such as an methyl group, an ethyl group, an i- or n-propyl group, a sec- or tert-butyl group, an n-pentyl group, a 2-methyl-butyl group, an n-hexyl group, a heptyl group, an octyl group, an nonyl group, a decyl group. Examples for branched alkyl groups include isopropyl, isobutyl, isopentyl, 2,2-dimethylpropyl, isohexyl, 3-methylpentyl, 2,2-dimethylbutyl, 2,3-dimethylbutyl, isoheptyl, 2-ethylbutyl, 3-methylhexyl, 2,2-dimethylpentyl, 2,3-dimethylpentyl, 2,4-dimethylpentyl, 2,2,3-trimethylbutyl, isooctyl, 3-methylheptyl, 4-methylheptyl, 2,2-dimethylhexyl, 2,4-dimethylhexyl, 2,5-dimethylhexyl, 2,2,3-trimethylpentyl, 2,2,4-trimethylpentyl, 2,2,5-trimethylpentyl and isononyl groups.

The residues $R^1$ and/or $R^2$ of a the substrate according to the general formula (1) can furthermore be selected among linear or branched lower alkenyl groups, which can be substituted at one or more positions. Examples comprise unsaturated analogues of lower alkyl groups, comprising one or more carbon-carbon double bonds at any possible position of the carbon chain. Examples are vinyl groups, allyl groups (2-propenyl), but-1-enyl groups, cis-but-2-enyl groups, trans-but-2-enyl groups, pent-1-enyl groups, cis-pent-2-enyl groups, trans-pent-2-enyl groups, 2-methyl-but-1-enyl groups, 2-methyl-but-2-enyl groups, 3-methyl-but-1-enyl groups, hex-1-enyl groups, hex-2-enyl groups both as cis- or trans-isomeres, hex-3-enyl groups, 2-methyl-pent-1-enyl groups, 2-methyl-pent-2-enyl groups, 3-methyl-pent-2-enyl groups, 4-methyl-pent-1-enyl groups, 4-methyl-pent-2-enyl groups, 2-ethyl-but-1-enyl groups, 2,3-dimethyl-but-1-enyl groups, 2,3-dimethyl-but-2-enyl groups, 3,3-dimethyl-but-1-enyl groups.

The residues $R^1$ and/or $R^2$ of a the substrate according to the general formula (1) can furthermore be selected among cyclic alkyl groups comprising compounds with a cyclic carbon backbone, in particular compounds with a cyclic carbon backbone of 3 to 10 carbon atoms, i.e. cyclopropyl, cyclobutyl, cyclopentyl, cyclohexyl, cycloheptyl, cyclooctyl, cyclononyl. Furthermore included are mono- or polyunsaturated analogues of cyclic alkyl groups, such as cyclo-butenyl groups, cyclopentenyl groups, cyclopentadienyl groups, cyclohexenyl groups, cycloheptenyl groups, cyclohexadienyl groups, and cycloheptadienyl groups. The cyclic alkyl groups or their mono- or polyunsaturated analogues may be substituted at one or more positions. The residues $R^1$ and $R^2$ of a the substrate according to the general formula (1) can furthermore be selected among mono- or polycyclic aryl groups, which may be substituted at one or more positions. Examples for aryl groups are mono- or polycyclic (in particular dicyclic) aromatic groups, in particular phenyl groups or naphthyl groups bonded via any carbon atom of the ring, for example 1-naphthyl and 2-naphthyl.

The residues $R^1$ and/or $R^2$ of a substrate according to the general formula (1) can furthermore be selected among mono- or polycyclic heteroaryl groups, which may be substituted at one or more positions. For example heteroaryl groups may be derived form pyrrolidine, tetrahydrofuran, tetrahydrothiophene, piperidine, tetrahydropyrane, tetrahydrothiopyrane, pyrimide, morpholine, pyrrole, furane, thiophene, pyrazole, imidazole, oxazole, thioazole, pyran, pyrimidine, pyridazine and pyrazine. Examples for dicyclic groups are condensates of the aforementioned aryl groups or heteroaryl groups, or their respective derivatives, with an additional aryl group, a heteroaryl group or their respective derivatives, such as groups derived from cumarole, indole, chinoline, purine and naphthalene. The mono- or polycyclic heteroaryl groups may be substituted at one or more positions, and may be linked to the respective carbon atom in the general formula (1) via any atom of the ring, preferentially via a carbon atom of the ring. Examples for suitable groups include 2-thienyl groups, 3-thienyl groups, 2-furanyl groups, 3-furanyl groups, 2-pyridyl groups, 3-pyridyl groups, 4-pyridyl groups, 2-thiazolyl groups, 4-thiazolyl groups, 5-thiazolyl groups, 4-methyl-2-thienyl groups, 3-ethyl-2-thienyl groups, 2-methyl-3-thienyl groups, 4-propyl-3-thienyl groups, 5n-butyl-2-thienyl groups, 4-methyl-3-thienyl groups, 3-methyl-2-thienyl groups, 3-chloro-2-thienyl groups, 4-bromo-3-thienyl groups, 2-iodine-3-thienyl groups, 5-iodine-3-thienyl groups, 4-fluoro-2-thienyl groups, 2-bromo-3-thienyl groups and 4-chloro-2-thienyl groups.

The residues $R^1$ and/or $R^2$ of the substrate according to the general formula (1) can furthermore be selected among linear or branched alkoxy groups, which optionally may be substituted at one or more positions. In this case the compound of the general formula (1) is linked via an oxygen atom with a group according to any of the aforementioned definitions, e.g. a linear or branched, optionally substituted, lower alkyl group; a linear or branched, optionally substituted, lower alkenyl group; an optionally substituted cyclic alkyl group; a mono- or polycyclic, optionally substituted aryl group (which may also be referred to a aryloxy group); a mono- or polycyclic, or an optionally substituted heteroaryl group. Examples for alkoxy groups are the methoxy group ($—O—CH_3$), the ethoxy group ($—O—C_2H_5$) and groups of the general formula $—O—C_nH_{2n+1}$, wherein n preferentially is an integer from 1 to 10.

The residues $R^1$ and/or $R^2$ of the substrate according to the general formula (1) can furthermore be selected among an amino group and linear or branched alkylamino groups, which optionally may be substituted at one or more positions. In this case the compound of the general formula (1) is linked via a nitrogen atom, which itself is linked to two hydrogen atoms (primary amine, amino group), one hydrogen and one organic residue (secondary amine, $—NHR^1$), or two organic residues (tertiary amine, $—NR^1R^2$), wherein the organic residues $R^1$ and $R^2$ independently from each other may be selected from any group according to the aforementioned definitions for linear or branched, optionally substituted, lower alkyl groups; linear or branched, optionally substituted, lower alkenyl groups; optionally substituted cyclic alkyl group; a mono- or polycyclic, optionally substituted aryl groups, and mono- or polycyclic, or an optionally substituted heteroaryl group. Examples for amino groups are the primary amino group ($—NH_2$). Examples for secondary amino groups are the methylamino group (—NH—CH3), the ethylamino group (—NH—C2H5) and groups of the general formula $—NH-CnH2n+1$, wherein n preferentially is an integer between 1 and 10. Examples for tertiary amino groups are the dimethylamino group ($—N(CH_3)_2$), the diethylamino group ($—N(CH_2CH_3)_2$), the dipropylamino group ($—N(CH_2CH_2CH_3)_2$), the dibutylamino group ($—N(CH_2CH_2CH_2CH_3)_2$), the methylethylamino group, the methylpropylamino group, and the like.

The residues $R^1$ and/or $R^2$ of the substrate according to the general formula (1) can furthermore be selected among linear or branched alkylthio groups, which optionally may be substituted at one or more positions. In this case the compound of the general formula (1) is linked via a sulfur atom with a group according to any of the aforementioned definitions, e.g. a linear or branched, optionally substituted, lower alkyl group; a linear or branched, optionally substituted, lower alkenyl group; an optionally substituted cyclic alkyl group; a mono- or polycyclic, optionally substituted aryl group (which may be referred to as thioaryl group); a mono- or polycyclic, or an optionally substituted heteroaryl group. Examples for alkylthio groups are the thiomethyl group ($-s-CH_3$), the thioethyl group ($—S—C_2H_5$) and groups of the general formula $—S—C_nH_{2n+1}$, wherein n preferentially is an integer from 1 to 10.

The residues $R^1$ and/or $R^2$ of the substrate according to the general formula (1) can furthermore be selected among linear or branched acyl groups, which optionally may be substituted at one or more positions. Acyl groups have the general formula $—C—C(O)—R$, wherein R may be any alkyl group, aryl group or heteroaryl group as defined herein. When R is hydrogen or OH, the group $—C(O)—R$ is an aldehyde group or a carboxyl group, respectively.

The aforementioned groups may optionally be substituted at one or more positions. The hydrogen atoms of the carbon atoms may for example independently from each other be substituted by further carbon compounds, such as linear or branched lower alkyl or alkenyl groups, cyclic alkyl groups, aryl or heteroaryl group, halogen, such as fluorine, chlorine, bromine and iodine, or heteroatoms or compounds containing heteroatoms. Examples for heteroatom containing compounds are $—OH$, $—SH$, $—NO_2$, $—NO_3$, $—NH_2$, $—SO_3$, $—SO_4$ groups, alkoxy groups and $NR^3R^4$, wherein $R^3$ and $R^4$ independently from each other represent H, a methyl group or an ethyl group.

In particular embodiments of the method according to the invention $R^2$ is H. In further preferred embodiments $R^2$ is H, and $R^1$ is concomitantly selected from H, a methyl group, an optionally substituted aryl group, in particular an optionally substituted monocyclic aryl group. Preferred examples are a phenyl group, a mono- or polysubstituted phenyl group, wherein the substitutents independently form each other may be selected from, e.g. a halogen, methyl, ethyl, $—OH$, $—NH_2$, $—NO_2$, and $—CO_3H$. The substituted phenyl group may, e.g., be 2-F—$C_6H_4$, 3-F—$C_6H_4$, 4-F—$C_6H_4$, 2-Cl—$C_6H_4$, 3-Cl—$C_6H_4$, 4-Cl—$C_6H_4$, 2,3-F—$C_6H_3$, 2,4-F—$C_6H_3$, 2,5-F—$C_6H_3$, 2,3-Cl—$C_6H_3$, 2,4-Cl—$C_6H_3$, 2,5-Cl—$C_6H_3$, and the like.

In further particular embodiments $R^2$ is H and $R^1$ is selected from the group comprising H, —$CH_3$, —$CH_2CH_2CH_2NH$—$C(NH)NH_2$, —$CH_2CONH_2$, —$CH_2COOH$, —$CH_2SH$, —$CH_2CH_2CONH_2$, —$CH_2CH_2COOH$, —$CH_2(C_3H_3N_2)$, wherein $C_3H_3N_2$ denotes an imidazole group, —$CH(CH_3)CH_2CH_3$, —$CH_2CH(CH_3)_2$, —$CH_2CH_2CH_2CH_2NH_2$, —$CH_2CH_2SCH_3$, —$CH_2(C_6H_5)$, —$CH_2OH$, —$CH(OH)CH_3$, —$CH_2(C_8H_6N)$, wherein $C_8H_6N$ denotes an indole residue, —$CH_2(C_6H_4)OH$, —$CH(CH_3)_2$, —$CH_2$—$SeH$, —$CH_2$—$CH_2$—$SeCH_3$ (Selenomethionin), —$(C_6H_5)$, p-F—$C_6H_4$, and p-Cl—$C_6H_4$.

C. Process Conditions

The at least one enzyme, selected among a hydantoinase and a dihydropyrimidinase, which is present during the method for producing a β-amino acid precursor, can be present in living cells naturally or recombinantly producing the enzyme or enzymes, in harvested cells, in dead cells, in permeabilized cells, in crude cell extracts, in purified extracts, or in essentially pure or completely pure form. The at least one enzyme may be present in solution or an enzyme immobilized on a carrier. One or several enzymes may simultaneously be present in soluble and immobilised form.

The method according to the invention can be performed in common reactors, which are known to those skilled in the art, and in different ranges of scale, e.g. from a laboratory scale (few millilitres to dozens of liters of reaction volume) to an industrial scale (several liters to thousands of cubic meters of reaction volume). If the hydantoinase and/or dihydropyrimidinase is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for upscaling chemical or biotechnological methods from laboratory scale to industrial scale, or for optimizing process parameters, which are also extensively described in the literature (for biotechnological methods see e.g. Crueger und Crueger, Biotechnologie—Lehrbuch der angewandten Mikrobiologie, 2. Ed., R. Oldenbourg Verlag, München, Wien, 1984).

Cells containing the at least one hydantoinase and/or dihydropyrimidinase can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like. If the at least one enzyme is immobilised, it is attached to an inert carrier. Suitable carrier materials are known in the art and are, e.g., disclosed in EP-A-1149849, EP-A-1 069 183 and DE-OS 100193773 as well as the literature references cited therein (all of which are specifically enclosed with regard to carrier materials). Examples for suitable carrier materials are clays, clay minerals such as kaolinite, diatomeceous erth, perlite, silica, alumina, sodium carbonate, calcium carbonate, cellulose powder, anion exchanger materials, synthetic polymers, such as polystyrene, acrylic resins, phenol formaldehyde resins, polyurethanes and polyolefines, such as polyethylene and polypropylene. For preparing carrier-bound enzymes the carrier materials usually are used in the form of fine powders, wherein porous forms are preferred. The particle size of the carrier material usually does not exceed 5 mm, in particular 2 mm. In case the at least one enzyme is present in a whole-cell-preparation, said whole-cell-preparation may be present in a free or immobilised form. Suitable carrier materials are e.g. Ca-alginate or Carrageenan. Enzymes as well as cells may directly be linked by glutaraldehyde. A wide range of immobilisation methods is known in the art (e.g. J. Lalonde and A. Margolin, "Immobilization of Enzymes" in K. Drauz und H. Waldmann, Enzyme Catalysis in Organic Synthesis 2002, Vol. III, 991-1032, Wiley-VCH, Weinheim).

D. Enzymes

The at least one enzyme to be used in the process for biocatalytic production of a β-aminoacid precursor, in particular for biocatalytic enantioselective production of a β-aminoacid precursor, is selected among a hydantoinase and a dihydropyrimidinase, preferentially any hydantoinase or any dihydropyrimidinase obtainable from *Vigna angularis*. During the biocatalytic production of a β-amino acid precursor one or several hydantoinases, one or several dihydropyrimidinases, or any combination thereof may be present. Preferentially, at least one hydantoinase is present. The at least one enzyme preferentially is an enantioselective enzyme, preferentially a D-dihydropyrimidinase and/or a D-hydantoinase. In particular the enzyme is a D-hydantoinase. The at least one enzyme is preferentially capable of producing the corresponding (S)—N-carbamoyl-β-amino acid by hydrolyzing a (±)-6-monosubstituted dihydrouracil, e.g. a (S)—N-carbamoyl-β-phenylalanine from (±)-6-phenyl dihydrouracil.

If the at least one enzyme is to be purified, common methods known to those skilled in the art can be used. After disruptions of cells crude extracts can be obtained by centrifugation or filtration, in particular for separation proteins from cell debris, membrane fragments or cell ghosts. Additional or alternative purifications steps comprise gel filtration, ion exchange chromatography (e.g. using Q-Sepharose), hydrophobic chromatography, reverse phase chromatography, ultrafiltration, crystallization, salting out, dialysis, native gelelectrophoresis, immuneprecipitation, affinity chromatography, and the like. Suitable methods are e.g. described in Cooper, F. G., Biochemische Arbeitsmethoden, Verlag Walter de Gruyter, Berlin, N.Y., or in Scopes, R., Protein Purification, Springer Verlag, New York, Heidelberg, Berlin. According to preferred embodiments the at least one enzyme is present in at least partially purified form or in essentially purified form. In the context of the present invention the enzymes are in an essentially purified form, if other proteins normally present in a cell or an organism used as source for the enzyme cannot be clearly detected by Coomassie staining after sodium dodecylsulfate polyacrylamide gelelectrophoresis (SDS PAGE), but may still be discerned as bands on an SDS PAGE gel after silver staining. Enzymes are present in completely pure form if bands of other proteins cannot or only faintly be discerned after SDS PAGE and subsequent silver staining. The isolation of hydantoinases has been described in the literature (e.g. Morin, Enzyme Microb. Technol. 15:208-214, 1993; Fan and Lee, Biochemical Engineering J. 8:157-164, 2001). Preferred extraction methods include at least three, in particular at least four, at least five, or all of the following steps, preferentially to be performed in the following sequential order:
a) ion exchange chromatography (e.g. using a Q-Sepharose FF-chromatography column)
b) hydrophobic chromatography (e.g using a phenyl sepharose column)
c) gel filtration (e.g. using a Superdex Prep Grade 200 Gel Filtration column)
d) affinity chromatography (e.g. using a Blue HiTrap 5 ml affinity chromatography column)
e) anion exchange chromatography (e.g. using a Mono Q HR 5/5 anion exchange column), and
f) gel filtration (e.g. using a Superose 6 prep grade gel filtration column).

Suitable sources for the at least one hydantoinase and/or dihydropyrmimidase are microorganisms and higher organisms, such as bacteria and archeabacteria, yeasts, fungi, plants and animals, fungi, yeasts, bacteria and archaebaceria. Examples for bacteria are *Acidovorax* (e.g. *A. avenae*); *Agrobacterium* (e.g. *A. radiobacter, A. tumefaciens*, A. sp IP I-671, *A. tumefaciens* RU-OR, and *A. tumefaciens* NRRL B 11291); *Arthrobacter* (e.g. *A. crystallopoietes* AM2), *Aurantimonas* (e.g. A. sp. SI85-9A1); *Brucella* (e.g. *B. canis, B. ceti, B. ovis, B. pinnipedialis, B. suis*); *Burckholderia* (e.g. B. sp. H160, *B. phymatum, B. phytofirmans*); *Dickeya* (e.g. *D. dadantii*); *Jannaschia* (e.g. J. sp. CCS1); *Mesorhizobium* (e.g. *M. loti*); *Oceanicola* (e.g. *O. batsensis*); *Ochrobactrum* (e.g. *O. intermedium*, O. sp. G21, *O. anthropi*); *Polaromonas* (e.g. *P. naphthalenivorans*), *Reinekea* (e.g. R. sp. MED297); *Rhizobium* (e.g. *R. leguminosarum*); *Verminephrobacter* (e.g. *V. eiseniae*); *Rhodobacter* (e.g. *R. sphaeroides*); *Vibrio* (e.g. *V. cholerae*); *Fulvimarina* (e.g. *F. pelagi*). An example for a simple metazoic organism is *Trichoplax adherens*, and examples for lower and higher plants are *Arabidopsis* (e.g. *A. thaliana*); *Bradyrhizobium* (e.g B. sp. ORS278; *B. japonicum*, B. sp. BTAi1); *Chlamydomonas* (e.g. *C. reinhardtii*); *Glycine* (*Glycine max*); *Medicago* (*M. trunculata*); *Oryza* (e.g. *O. sativa*); *Physcomitrella* (e.g. *P. patens*); *Picea* (e.g. *P. sitchensis*); *Populus* (e.g. *P. trichocarpa*); *Ricinus* (e.g. *R. communis*); *Sorghum* (e.g. *S. bicolor*); *Vitis* (e.g. *V. vinifera*); *Zea* (e.g. *Zea mays*). Examples for animals are *Gallus* (e.g. *G. gallus*); *Homo sapiens; Macaca* (e.g. *M. mulatta*); Pan (e.g. *P. troglodytes*), and *Xenopus* (e.g. *X. laevis, X. tropicalis*).

Particularly preferred sources of the at least one hydantoinase and/or dihydropyrimidinase are the genera *Vigna* (in particular *Vigna angularis*), *Agrobacterium, Arthrobacter* and *Pseudomonas* (in particular *Burckholderia* according to recent taxonomy). Hydantoinase from *Vigna angularis* is commercially obtainable from Sigma-Aldrich (Sigma-Aldrich Corp., St. Louis, Mo., USA).

Particularly preferred are hydantoinases and/or dihydropyrimidinases, which comprise at least one partial sequence having an identity of between 60 percent and 100 percent to at least one of the following partial sequences:

```
IELGITGPEGQRLAGPTVL      (SEQ ID NO: 1)

IELGITGPEGQRLAGPVL       (SEQ ID NO: 2)

IELITGPEGQRLAGPTVL       (SEQ ID NO: 3)

IELITGPEGQRLAGPVL        (SEQ ID NO: 4)

EEIARARKSGQRVIGEPVAS     (SEQ ID NO: 5)

ITGPEGQRLAGP.            (SEQ ID NO: 7)
```

The degree of identity with any of SEQ ID NO:1-5 or 7 can be at least 60%, at least 65%, at least 70%, at least 75%, at least 80%, at least 85% or at least 90%. In particular, the degree of identity with any of SEQ ID NO:1-5 or 7 can be at least 91%, at least 92%, at least 93%, at least 94%, at least 95%, at least 96%, at least 97%, at least 98% or at least 99%. In particular, any of SEQ ID NO:1-5 or 7 may be identical to a sequence comprised in a hydantoinase and/or dihydropyrimidinase (100% identity). The hydantoinase and/or dihydropyrimidinase character of any given protein may easily be determined by the hydantoinase and/or dihydropyrimidinase assays described in this specification.

In addition or as alternative to hydantoinases and/or dihydropyrimidinases present in organisms or microorganisms or extracted thereof, functional equivalents of those hydantoinases and/or dihydropyrimidinases may be used.

Functional equivalents are mutants which in at least one position differ from the natural amino acid sequence while still retaining at least partially the enzymatic activity of a hydantoinase and/or dihydropyrimidinase. Functional equivalents may comprise one or more, as for example 1 to 20, 1 to 15 or 1, 2, 3, 4, 5, 6, 7, 8, 9 or 10 amino acid additions, substitutions, deletions and/or inversion, which may occur at any sequence position as long as they do not completely abolish the catalytic activity. Functional equivalents may also be enzymes with altered turnover speed of substrate and/or product, altered affinity for substrate and/or product, and/or altered selectivity of particular substrates (e.g. functional equivalents accepting substrates with more bulky or hydrophobic groups $R^1$ and/or $R^2$). Non-limiting examples for substitutions with high probability of at least partially preserving the enzymatic activity are listed below:

| original amino acid residue | possible substitution by |
|---|---|
| Ala | Ser; Gly; Val |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Functional equivalents furthermore comprise precursors of mature hydantoinase and/or dehydropyrimidinase proteins as well as salts thereof. Salts comprise salts of carboxyl groups and acid addition salts of amino groups. Salts of carboxyl groups may be produced according to methods known in the art and comprise inorganic salts, such as sodium, calcium, ammonia, iron and zinc salts, as well as salts formed with organic bases such as amines, e.g. triethanol amine, arginine, lysine, piperidin and the like. Acid additions salts comprise salts with mineral acids, such as hydrochloric acid or sulphuric acid, and salts formed with organic acids, such as acetic acid and oxalic acid.

Functional equivalents may also be obtained by modifying naturally occurring hydantoinases and/or dihydropyrimidinases at one or more amino acid side chains or the N- or C-termini. Such derivatives may for example comprise aliphatic esters of carboxyl groups, amides of carboxyl groups, obtainable by reaction with ammonia or a primary or secondary amine, N-acyl derivatives or free amine groups, obtainable by reaction with acyl groups, or O-acyl derivatives of free hydroxyl groups, obtainable by reaction with acyl groups. Also included are functional equivalents obtainable by a glycosylation pattern differing from the natural pattern (e.g. after artificial glycosylation or deglycosylation).

Functional equivalents furthermore comprise enzymes obtained from other organisms or microorganisms, as well as naturally occurring variants of the reference enzyme.

Functional equivalents furthermore comprise single domains or sequence motives having the desired activity of hydantoinases and/or dihydropyrimidinases.

Moreover, functional equivalents may be fusion proteins comprising naturally occurring sequences or functional equivalents thereof in combination with at least one functionally different sequence in N-terminal or C-terminal linkage, which do not abolish the hydantoinase and/or dihydropyrimidinase activity of the protein. Non-limiting examples for such functionally different sequence are signalpeptides (e.g. directing the excretion of the fusion protein), enzymes (e.g. for adding additional enzymatic activities) or parts of immuneglobulins (e.g. for immobilising the fusion protein).

Functional equivalents also comprise homologues of the naturally occurring proteins. Said homologues have a homology of at least 60%, preferentially at least 75%, and in particular at least 85%, such as 90%, 95% or 99% compared to a naturally occurring amino acid sequence (as calculated by the algorithm of Pearson and Lipman, Proc. Natl. Acad, Sci. (USA) 85(8), 1988, 2444-2448). "% homology" of a given polypeptide in particular denotes the percentage of identity of the amino acid residues in relation to the total length of the reference enzyme or enzyme subunit.

Functional equivalents may also be produced by methods known in the art. Methods for the modification of genes and consequently for the proteins encoded by those genes have been known for a long time, such as site directed mutagenesis, where single or multiple nucleotides of a gene are specifically exchanged (Trower M K (Hrsg.) 1996; In vitro mutagenesis protocols. Humana Press, N.J.), saturation mutagenesis, allowing the exchange or addition of a codon for any amino acid at any position of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Bank S (1995) Mol Biotechnol 3:1), error-prone polymerase chain reaction (error-prone PCR), wherein nucleotide sequences are mutated by DNA polymerases, which do no work error-free (Eckert K A, Kunkel T A (1990) Nucleic Acids Res 18:3739); the passaging of genes in mutator strains, in which an increased mutation rate is observer, e.g. due to defective DNA repair mechanisms (Greener A, Callahan M, Jerpseth B (1996) An efficient random mutagenesis technique using an *E. coli* mutator strain. In: Trower M K (Hrsg.) In vitro mutagenesis protocols. Humana Press, N.J.), or DNA shuffling, wherein first a pool of closely related genes is formed and digested, and subsequently the obtained fragments are used as templates for a polymerase chain reaction, wherein full length mosaic genes are created by repeated strand separation and annealing (Stemmer W P C (1994) Nature 370:389; Stemmer W P C (1994) Proc Natl Acad Sci USA 91:10747).

Depending on the method applied those skilled in the art may introduce either purely random or more directed mutations into genes or non-coding regions (which may be relevant for the regulation of expression) and subsequently create gene banks. The methods required are known to those skilled in the art, and are described, e.g., in Sambrook und Russell, Molecular Cloning. 3. Edition, Cold Spring Harbor Laboratory Press 2001.

When methods of so-called "directed evolution" (as described, among others, in Reetz M T und Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Hrsg.) Manual of industrial microbiology and biotechnology. American Society for Microbiology) are applied, functional equivalents may be created in a directed (as opposed to purely random) approach and in large scale. In a first step gene banks of the respective proteins (such as hydantoines and/or dihydropyrimidinases) are created, for example by applying the aforementioned methods. The gene banks are expressed in a suitable way, e.g. by bacteria or phage display systems. Moreover, methods for controlling the localization of a protein in a host by selecting suitable expression vectors are known in the art. Proteins may be localized intracellularly in the cytoplasm, in membranes upon addition of a membrane anchor, or extracellularly by addition of a signal peptide containing a recognition sequence for a signal peptidase. In a subsequent second step clones, which express proteins with a desired characteristic, are selected or screened. If a selection method is used, clones expressing proteins with desired characteristics will survive, as those proteins will facilitate or ensure the survival of the host cells (e.g, enzymes, which allow the use of particular substrates or growth at particular temperatures). If a screening method is used, all clones will survive. Clones expressing a protein with a desired characteristic are identified using suitable assays, which easily can be devised by those skilled in the art. When searching, e.g., for proteins with particular binding characteristics, host cells can be screened for, which attach to a surface coated with a substrate for the desired binding capability. Host cells expressing such a protein can attach to the substrate via the expressed protein, while host cells expressing non-functional proteins are unable to do so. When screening for functional equivalents with particular catalytic characteristics, host cells may be cultivated in substrate-containing medium or on substrate-containing agar plates. The presence of functional equivalents may, e.g., be indicated by colour changes after modification of the substrate by such functional equivalents (if necessary, after lysis of the host cells in order to allow the contact of the functional equivalents with the substrate-containing medium). Functional equivalents of hydantoinase or dihydropyrimidinases may be screened by media containing dihydrouracils with substitutions of interest.

In this context automated systems (e.g. pipetting robots for microtiter plates, screening robots, image processing systems for identifying colonies on agar plates) may be used in order to allow a high-throughput screening. The respective genes of host cells which express functional equivalents having characteristics, which largely or at least partially, correspond to the desired characteristics, are subjected to one or more rounds of mutation. The steps of mutating and selecting or screening may be repeated in an interactive process until the functional equivalents have the desired characteristic to a satisfactory degree.

By applying an iterative approach it is possible to screen for proteins with desired characteristics in a directed approach, although by inserting numerous mutations into a protein sequence a loss of function is more likely than improving a given characteristic (such as turnover rate of an enzyme) or gaining a new characteristic (such as accepting new substrate classes). When implementing the iterative approach a gene library with mutations is created based on the nucleotide sequence of a reference protein, such as a wildtype protein (e.g. a particular hydantoinase or dihydropyrimidinase). In this context the chosen mutation rate on nucleotide level will cause a relatively low number of amino acids to be mutated in the corresponding translated peptides or proteins, e.g. 1 to 3 amino acids. The resulting peptides or proteins are subsequently screened for the desired feature (e.g. a higher catalytic activity for one or more substrates, an expanded or altered substrate range, increased stability at increased or changed temperatures or pH values, or in the presence of particular solvents). Based on the sequences of proteins or peptides with such desired characteristics (which may only be evident to a low degree), a second gene library is created, and again a low rate of mutations is introduced. Subsequently the translated proteins are screened for the desired characteristic. The cycle of creating a mutated gene library and screening the peptides or proteins expressed on the basis of the library can be repeated as often as deemed necessary. Choosing a low mutation rate per cycle will prevent a situation, where virtually all proteins are non-functional because of the accumulation of too many mutations. The low mutation rate (and concomitantly the low or slow manifestation of desired characteristics) can be compensated by iteratively repeating mutation (possibly leading to functional equivalents) and selection (of desirable functional equivalents), thereby leading to an accumulation of useful mutations, and ultimately providing with a high rate of success proteins with desired, improved characteristics. By sequence analysis of functional equivalents with improved characteristics sequence information can be obtained which identify sequence positions or sequence areas within a peptide or protein, which are important for a desired characteristic. Examples for the creation of proteins with desired characteristic, from which also further methods for introducing mutations will become obvious, are described in Zhao and Arnold, Protein Engineering 12:47-53 (1999) or May et al., Nature Biotechnology 18:317-320 (2000).

Functional equivalents may also be obtained by nucleic acid sequences derived form the nucleic acid sequences underlying the proteins described above. Unless further specified, a nucleic acid sequence derived from an original nucleic acid denotes a nucleic acid sequence having an identity compared to the original nucleic acid of at least 80% or at least 90%, in particular about 91%, 92%, 93%, 94%, 95%, 96%, 97%, 98% or 99%. 100% identity denotes the identity of nucleotides of two nucleic acid sequences over the whole nucleic acid length, in particular an identity determined by comparison of both nucleic acid sequences using the Vector NTI Suite 7.1 software of Infomax (USA) and the Clustal method.

Derived nucleic acids (single strand or double strand DNA or RNA sequences, as cDNA or mRNA) may be chemically synthesized from nucleotide building blocks by methods known in the art, e.g. by condensation of nucleotide building blocks or oligomers. For example, chemical synthesis may occur via the phosphoamidite method (Voet, Voet, 2. Ed., Wiley Press, New York, p. 896-897). The annealing of synthetic oligonucleotides and the filling of gaps using the Klenow fragment of DNA polymerase, ligation reactions as well as general cloning methods are known in the art and are described, e.g. in Sambrook et al., Molecular Cloning: A laboratory manual, Cold Spring Harbor Laboratory Press, 1989.

Derived nucleic acids may be identified in databases or isolated from gene banks or organisms. In particular, derived nucleic acids may be isolated by using the nucleic acids corresponding to the peptide sequences according to SEQ ID NO:1-5 or 7 as probes for hybridisation or as primers for polymerase chain reaction (PCR). The probes or primers usually comprise a nucleotide sequence region, which under stringent conditions hybridises to at least 12, preferentially at least 25, such as about 40, about 40 or about 75 consecutive nucleotides of the sense strand or antisense strand of a potential derived nucleic acid sequence. The potential derived nucleic acid sequence may be present in gene banks, in cellular material of a target organism, e.g. cells (preferentially permeabilised cells) or cell components extracted thereof (preferentially at least partially purified nucleic acids), wherein the target organism is a organism to be examined for the presence of derived nucleic acids. The cellular material may be separated on agarose gels and be transferred to membranes for performing Northern Blot or Southern Blot hybridisation under standard conditions in order to detect the presence of nucleic acid fragments binding to the probes used, or may alternatively serve as template for primers in PCR reactions, wherein the probes or primers may be derived from nucleic acids sequences underlying any of the peptide sequences according to SEQ ID NO:1-5 or 7. Hybridising nucleic acid bands on blot membranes or gels, or hybridising template nucleic acids in PCR reactions (which may be amplified using forward or reverse primers derived from the original nucleic acid, or random primers) can be isolated and cloned in to suitable vectors according to methods generally known in the art (e.g. Sambrook et al., 1989), and subsequently be sequenced or used as hybridisation probes under even more stringent conditions in order to isolate nucleic acid fragments containing longer or preferentially full-length genes from gene banks or cellular material.

Standard conditions for hybridisation vary depending on the respective nucleic acid and generally comprise temperatures from 42° C. to 58° C. in an aqueous buffer solution of 0.1×SSC to 5×SSC (wherein 1×SSC corresponds to 0.15 M NaCl, 14 mM sodium citrate, pH 7.2), or additionally in presence of 50% formamide, such as 42° C. in 5×SSC containing 50% formamide. The hybridisation conditions for DNA:DNA hybrids preferentially comprise 0.1×SSC and temperatures from about 20° C. to about 45° C., in particular 30° C. to 45° C. The hybridisation conditions for DNA:RNA hybrids preferentially comprise 0.1×SSC and temperatures from about 30° C. to about 55° C., in particular 45° C. to 55° C. The aforementioned temperatures are exemplary temperatures for the hybridisation of a nucleic acid containing about 100 nucleotides and a G+C content of 50% in an SSC buffer without formamide. The experimental conditions for DNA hybridizations and further techniques of molecular biology are described in textbooks or laboratory manuals of molecular biology (e.g. Sambrook et al., 1989, Ausubel et al. (eds.), Current Protocols in Molecular Biology, John Wiley & Sons, New York, 1985; Hames and Higgins (eds.), Nucleic Acid Hybridisation: A Practical Approach, IRL Press at Oxford University Press, Oxford, 1985; Brown (ed.), Essential Moelcular Biology: A Practical Approach, IRL Press at Oxford University Press, Oxford, 1991)), and can be calculated by those skilled in the art according to formulae generally known in the art, taking into consideration parameters such as the nucleic acid length, the type of hybrids and the G+C content. Examples for stringent conditions, e.g. in Northern Blots, comprise the use of 0.1×SSC containing 0.1% SDS (20×SSC: 3 M NaCl, 0.3 M sodium citrate, pH 7.0) and temperatures from 50° C. to 70° C., preferentially 60° C. to 65° C. for the elution of unspecifically bound probes or oligonucleotides. The choice and adaptation of stringent conditions is known in the art and described in the literature (e.g. Sambrook et al., 1989).

Derived nucleic acids may be isolated according to methods known in the art. Isolated nucleic acid molecules are to be understood as nucleic acid molecules essentially separated from other nucleic acid molecules comprising deviating sequences. Isolated nucleic acids molecules preferentially are essentially devoid of non-nucleic acid cell material or culture medium, or are essentially devoid of chemical precursors or other chemicals when produced by chemical synthesis.

Derived nucleic acids may be introduced into expression constructs, optionally after cleavage by restriction enzymes or ligations with linker molecules. In the expression constructs the derived nucleic acids are operatively linked with regulating elements controlling the expression of the corresponding polypeptide or protein sequence from the nucleic acid sequence, said nucleic acid sequence being a coding sequence for a useful hydantoinase or dehydropyrimidinase. The expression constructs preferentially comprise a promoter upstream of the derived nucleic acid and a terminator sequence downstream thereof, as well as optionally further regulatory elements. Operative linkage is to be understood as the sequential arrangement of promoter, coding sequence, terminator and, optionally, further regulatory elements in a way which allows the proper function of each of the aforementioned regulatory elements with respect to the expression of the coding sequence. Examples for elements to be operatively linked comprise targeting sequences, enhancers, polyadenylation signals, and the like. Further useful elements comprise selectable markers, amplification signals, replication origins and the like. Useful regulatory elements are known in the art and are described e.g. in Goeddel, Gene Expression Technology: Methods in Enzymology 185, Academic Press, San Diego, Calif. (1990). In addition to or instead of artificial regulatory elements or sequences the natural regulatory sequence upstream of the structural gene of a hydantoinase or dihydropyrimidinase may be present. The natural regulation may be switched off or modified for lower or higher expression by genetic modification. Likewise, the gene construct may also have a more simplified construction by just preserving the natural regulatory elements without inserting artificial ones. The natural regulatory elements may be mutated in such way that no regulation occurs and gene expression is lower or—preferentially—increased. The structural genes of hydantoinases or dihydropyrimidinases may be present as single or multiple copies, optionally mixed copies, i.e. hydantoinases and dihydropyrimidinase simultaneously present, in a gene construct.

Examples for useful promoter are cos-, tac-, trp-, tet-, trp-tet-, lpp-, lac-, lpp-lac-, lacIq-, T7-, T5-, T3-, gal-, trc-, ara-, SP6-, lambda-PR- or lambda-PL-promoters, which preferentially are used in gram negative bacteria; as well as the promoter amy and SPO2, or the yeast promoters ADC1, MFalpha, AC, P-60, CYC1, GAPDH. Inducible promoters may optionally be used, such as promoters inducible by temperature or chemical compounds (e.g. the metallothioenin promoter), allowing the induction of hydantoinase or dihydropyrimidinase expression after cell proliferation and accumulation of suitable cell densities. Likewise, artificial promoters may be used.

The recombinant expression construct is preferentially inserted into a suitable vector, e.g. a plasmid, which in turn is introduced into a suitable host cell. Vectors are known in the art and are described e.g. in Pouwels et al. (eds.), Cloning Vectors, Elsevier, Amsterdam-New York-Oxford, 1985). In addition to plasmids vectors may be all further vectors known in the art, such as phages, viruses, e.g. SV40, CMV, baculovirus and adenovirus, transposons, IS elements, phasmids, cosmids, and linear or circular DNA. The vectors may be autonomously replicated in the host, or may be chromosomally replicated after integration in the chromosome. Examples for non-fusion protein expression vectors are pTrc (Amann et al., (1988) Gene 69:301-315) and pET 11d (Studier et al. Gene Expression Technology: Methods in Enzymology 185, Academic Press, San Diego, Kaliformien (1990) 60-89). Examples for yeast expression vectors, e.g. for expression in *Saccharomyces cerevisiae* are pYepSec1 (Baldari et al., (1987) Embo J. 6:229-234), pMFa (Kurjan und Herskowitz (1982) Cell 30:933-943), pJRY88 (Schultz et al. (1987) Gene 54:113-123) and pYES2 (Invitrogen Corporation, San Diego, Calif.). Vectors and methods for the construction of vectors useful for fungi, in particular filamentous fungi, are describe in van den Hondel, C. A. M. J. J. & Punt, P. J. (1991) "Gene transfer systems and vector development for filamentous fungi, in: Applied Molecular Genetics of Fungi, J. F. Peberdy et al., Hrsg., S. 1-28, Cambridge University Press: Cambridge. Examples for bacalovirus vectors for expression of proteins in insect cells, such as Sf9 cells, comprise the pAc series (Smith et al., (1983) Mol. Cell. Biol. 3:2156-2165) and the pVL series (Lucklow und Summers (1989) Virology 170: 31-39), examples for mammalian cell vectors comprise pCDM8 (Seed, B. (1987) Nature 329:840) and pMT2PC (Kaufman et al. (1987) EMBO J. 6:187-195). Further expression systems for prokaryotic and eukarytic cells are described in chapters 16 and 17 of Sambrook, Fritsch, and Maniatis, Molecular cloning: A Laboratory Manual, $2^{nd}$ Ed., Cold Spring Harbor Laboratory, Cold Spring Harbor Laboratory Press, Cold Spring Harbor, N.Y., 1989.

Using the aforementioned vectors recombinant organisms can be produced which are transformed with at least one of those vectors and express a hydantoinase or dihydropyrimidinase useful for the methods according to the invention. The recombinant constructs can be expressed after introduction into a suitable host system. For introduction methods known in the art can be used, such as co-precipitation, protoplast fusion, electroporation, chemical transformation, retroviral transformation, and the like. Suitable methods are e.g. described in Current Protocols in Molecular Biology, F. Ausubel et al., ed., Wiley Interscience, New York 1997, oder Sambrook et al. Molecular Cloning: A Laboratory Manual. 2. Aufl., Cold Spring Harbor Laboratory, Cold Spring Harbor Laboratory Press, Cold Spring Harbor, N.Y., 1989.

Suitable host organisms or host cells are those which allow the expression of the nucleic acids coding for hydantoinases or dihydropyrmindinase, or nucleic acids derived thereof. Host cells comprise bacteria, fungi, yeasts, plant or animal cells. Examples for bacteria are those of the genera *Escherichia*, wie z. B. *Escherichia coli, Streptomyces, Bacillus, Pseudomonas* oder *Burkholderia*, examples for eukaryotic microorganismes are *Saccharomyces cerevisiae, Aspergillus*, higher eukaryotic cells from animals or plants, e.g. Sf9-, CHO- or HEK293 cells, wherein single cells or aggregated cells of higher eukaryotic life forms such as animals or plants herein also may be referred to as microorganisms.

The selection of successfully transformed cells may be based on marker genes contained in the respective vector or expression cassette. Examples for marker genes comprise genes for antibiotic resistance or for enzymes catalysing a colour forming reaction, which causes the staining or the fluorescence of the transformed cell. Said cells can be selected by automatic cell sorting. Successfully transformed cells carrying a antibiotic resistance gene, e.g. for G418 or hygromycin, can be selected by antibiotic containing media or agar plates. Marker proteins expressed on the cell surface can be used for selection via affinity chromatography.

The cells are cultivated as described in Chapter C above, and may excrete the hydantoinase or dihydropyrimidinase into the medium (thus allowing cells growth or survival and simultaneous biocatalytic production of a β-amino acid precursor from the at least one substrate of the general formula (1). In case the hydantoinase or dihydropyrimidinase is not secreted into to medium, the cells may be permeabilised after growth and/or induction of hydantoinase or dihydropyrimidinase expression in order to initiate the biocatalytic production of a β-amino acid precursor. Alternatively the cells may be harvested after growth and induction of hydantoinase or dihydropyrimidinase expression for partial or complete purification of the hydantoinase or dihydropyrimidinase, whereupon the purified hydantoinase or dihydropyrimidinase can be used for the biocatalytic production of a β-amino acid precursor.

E. Additional Process Steps

During the method for obtaining a β-amino acid precursor or a β-amino acid, one or more additional enzymes can optionally be present during the reaction. These enzymes catalyse the conversion between the D- and L-enantiomers of dihydrouracil substrates according to the general formula (I). Examples for suitable enzymes comprise dihydrouracil dehydrogenase (e.g. from mammalian sources), dihydrouracil oxidase (*Rhodotorula glutinis*) and enoate reductase (Old yellow enzyme).

The β-amino precursor according to the general formula (II) (β-amino acid carbamoyl derivative), which is produced by the method of the present invention, can be cleaved into the corresponding β-amino acid and the N-carbamoyl moiety while remaining in the reaction mixture. Alternatively, the β-amino acid precursor can be separated from the reaction mixture containing the substrate of the general formula (I) and the at least one hydantoinase and/or dihydropyrimidinase, and be cleaved to yield the β-amino acid. The cleavage can be performed chemically or enzymatically. Chemical cleavage can be achieved by adding an equimolar amount $NaNO_2$ to the β-amino acid precursor according to the general formula (II) at an acidic pH, e.g. 1.0 (e.g. as described by Fan and Lee, Biochemical Engineering Journal 8: 157-164, 2001). The acidic pH can be achieved by, e.g. sulphuric acid. The cleavage reaction can be performed at low temperatures, e.g. on ice. If the cleavage of the β-amino acid precursor of the general formula (II) is to be achieved chemically, it is preferred to perform this reaction separate from the enzymatic reaction leading from the substrate according to the general formula (I) to the β-amino acid precursor. The cleavage can be performed after the enzymatic conversion has been competed or come to an equilibrium (temporal separation), or in a different reaction vessel after removing of the reaction medium containing the β-amino acid precursor (spatial separation). As alternative to this batch method a continuous production can be achieved by contacting reaction medium containing the substrate molecule according to the general formula (I) with immobilized enzymes (hydantoinase and/or dihydropyrimidinase), which thereby are retained in the reactor vessel, whereas substrate-depleted reaction medium can be separated for cleavage of the β-amino acid precursor and simultaneously be replaced by fresh reaction medium. Enzymatic cleavage can be performed by enzymes such as carbamoylases (e.g. E.C.3.5.1.77 or E.C.3.5.1.87) or β-ureidopropionases (e.g. E.C.3.5.1.6). Said enzymes may be obtained by commercial suppliers (e.g. carbamoylase by Julich Chiral Solutions, Julich, Germany).

F. pH Values and Buffer Systems

The method according to the invention for converting a substrate according to the general formula (1) into a β-amino acid precursor according to the general formula (2) is preferentially performed at a pH from about 7.0 to about 11.0, preferentially at a pH from about 7.5 to 10.0. In particular, the pH is in the range from 7.5 to 8.5, more particular in the range from about 7.5 to 8.0. Particularly preferred pH values are about 7.5, 7.6, 7.7, 7.8, 7.9 and 8.0.

Any buffer suitable for the aforementioned pH values or pH ranges can be used, e.g. phosphate buffer, borate buffer and Tris buffers. In a pH range from 7.5 to 9.0 Tris buffers are preferred, while phosphate buffers are useful in a pH range from 6.0 to 8.0. Especially preferred are reaction solutions buffered by Tris. The concentration of the buffer can be determined depending on the concentration of substrate used, and preferentially is in the range from 1 mM to 200 mM, e.g. 1 mM to 100 mM, 1 mM to 50 mM. In particular the buffer concentration may be from 2 mM to 25 mM or 3 mM to 10 mM, such as 5 mM.

G. Temperature and Duration of the Reaction

The process for biocatalytic conversion of a substrate of the general formula (I) can be performed at any temperature which is tolerable for the hydantoinase and/or dihydropyrimidinase used. The temperatures usually correlate with the optimal growth temperatures of the organisms or microorganism harbouring the enzyme(s) or used as source for their extraction, but can easily determined by those skilled in the art. In general, the process can be performed at temperatures from 30° C. to 60° C., in particular from 40° to 50° C. Examples for reaction temperatures are about 30° C., about 35° C., about 37° C., about 40° C., about 45° C., about 50° C., about 55° C. and about 60° C.

The process may proceed until an equilibrium between the substrate of the general formula (I) and the β-amino acid precursor of the general formula (2) is achieved, but may be stopped earlier. Usual process times are in the range from 1 minute to 25 hours, in particular 10 min to 6 hours. Preferred reaction times are in the range from 1 hour to 4 hours, in particular 1.5 hours to 3.5 hours.

H. Additional Components in the Reaction Medium

In order to increase the solubility of substrates with essentially hydrophobic $R^1$ and/or $R^2$, one or more organic co-solvent(s) can be included in the reaction medium.

Alternatively, the reaction can be performed in biphasic systems comprising aqueous and non-aqeuous phases. Examples for suitable solvents for the non-aqueous phase are aliphatic hydrocarbons, preferentially comprising 5 to 8 carbon atoms, such as pentane, cyclopentane, hexane, cylcohexane, heptane, octane or cyclooctane, halogenated aliphatic hydrocarbons, preferentially comprising one or two carbon atoms, such as dichloromethane, chloroform, tetrachloromethane, dichloroethane, aromatic hydrocarbons, such as benzene, toluene, xylenes, chlorobenzene or dichlorobenzene, aliphatic acyclic or cyclic ethers, preferentially comprising 4 to 8 carbon atoms, such as diethyl ether, methyl-tert-butylether, ethyl-tert-butylether, dipropyl ether, diisopropyl ether, tetrahydrofurane, or esters, such as ethylacetate or n-butyl acetate, or ketones, such as methyl-isobutylketone or dioxane, or mixtures thereof.

In particular embodiments the reaction medium is an aqueous reaction medium containing organic co-solvents, especially as a monophasic system. Examples for suitable co-solvents are butane-2-ol, methyl-tert-butyl ether (MTBE) and dimethylsulfoxide (DMSO). If MTBE is to be used, a concentration below the saturation in aqueous medium (approximately 12 vol.-%) is preferred, e.g. about 6%, about 5%, about 4%, about 3%, about 2%, about 1% or less than 1%.

MTBE can be used up to the saturation concentration in aqueous media (about 6 vol.-%), while DSMO can be used up to concentrations of about 2 vol.-% for increasing the solubility of the substrate without essentially interfering with the process yield.

I. Recovery of N-Carbamoyl β-Amino Acids or β-Amino Acids

Methods for isolating amino acids and N-carbamoyl amino acids from the reaction medium are known in the art and comprise techniques such as gel filtration, HPLC, reverse phase chromatography and ion exchange chromatography. Ion exchange chromatography, in particular anion exchange chromatography is a preferred method. Suitable ion exchange matrices comprise strong anion exchangers (e.g. Q Sepharose, based on quaternary ammonium) and weak anion exchangers (e.g DEAE Sepharose, based diethylaminoethyl). Examples for preferred methods are anion exchange chromatography using DEAE columns, or extraction with an organic solvent, using ethyl acetate to extract substrate, followed by 2-butanol to extract product from biotransformation.

The invention will now be shown in detail by the following examples which illustrate the invention, but are not intended to limit the invention.

EXAMPLES

Chemical Experiments

TLC was performed using plastic backed plates coated with 0.2 mm thick silica gel 60F254 (Mackerey-Nagel). Plates were visualised using U.V. light (254 nm) or permanganate dip. Chemicals were purchased from Sigma-Aldrich, Acros or Fluka unless otherwise stated. All reagents were standard laboratory grade and solvents anhydrous, and used as supplied unless otherwise stated. $^1$H-NMR and $^{13}$C-NMR were recorded on a Bruker AC300 or AC400 spectrometer. The following abbreviations are used: δ, chemical shift; bs, broad singlet; d, doublet; dd, doublet of doublets; J, coupling constant; m, multiplet; q, quartet; qui, quintet; s, singlet; sep, septet. Chemical shifts (δ) are reported in parts per million (ppm) and coupling constants (J) in Hz. Residual protic solvent, DMSO-d6 (δ H 2.50, qui) was used as the internal standard in 1H NMR spectra, and 13C NMR shifts were referenced using DMSO-d6 (δ C 39.5, sep) with broad band decoupling.

Biotransformation Experiments

Unless otherwise stated all experiments were carried out on a 5 mM scale of 6-PDHU (4.75 mg) in 5 mL tris buffer (0.1 M pH 7.5) with 1U of commercially available hydantoinase from *Vigna angularis* (35 mg, obtained from Sigma, St. Louis, USA) in 15 mL Falcon tubes, incubated in a thermomixer (Falcon) at 750 rpm and a temperature of 50° C.

Biotransformations were carried out using 1 Unit/reaction', in which 1 Unit is defined as the amount that will catalyse the formation of 1 µmole of N-carbamoyl-glycine per minute, from hydantoin.

Example 1

Assays for Hydrolysis of 5-Substituted Hydantoin or 6-Phenyldihydrouracil

In order to determine hycantoinase activity, D-hydantoinase (10.5 mg) was added to 5-phenylhydantoin (1.32 mg) dissolved in borate buffer (1.5 mL, 0.1 M, pH 9.0). The biotransformation was incubated in an Eppendorf "Themomixer comfort", (40° C., 1400 rpm). At given time points, aliquots (100 µL) of the mixture were taken and the reaction stopped by denaturing the enzyme and precipitating the soluble protein by addition of TCA, (12% w/v, 175 µL). After centrifugation the supernatant was collected and analysed by HPLC, wherein the following parameters were used:
Column: Agilent Zorbax XBD-C18 4.6 mm×50 mm, 3.5 µm. Conditions: 25° C., 1 ml/min of H$_2$O:acetonitrile, 85:15 (+0.1% TFA)
Retention times of 5-phenylhydantoin (3.6), N-carbamoyl-α-phenylglycine (2.7). The assay setup can be used to determine the hydantoinase activity of an enzyme suspected of having such activity by replacing D-hydantoinase by said enzyme.

In order to determine dihydropyrimidinase activity, D-hydantoinase (10.5 mg) was added to 6-phenyldihydrouracil, (1.14 mg) dissolved in Tris buffer (300 µL, 0.1 M, pH 7.5). The biotransformation was incubated in an Eppendorf "Themomixer comfort", (40° C., 1400 rpm). At given time points, aliquots (100 µL) of the mixture were taken and the reaction stopped by denaturing the enzyme (95° C., 5 min) =and precipitation of soluble proteins by addition of methanol (300 µL). After centrifugation the supernatant was collected and analysed by HPLC, wherein the following parameters were used: c-18 rpHPLC: isocratic mobile phase, 25° C., H$_2$O: ACN, 90:10+0.1% TFA
Retention times: 6-phenyldihydrouracil (12.6), N-carbamoyl-β-phenylalnine (NCBPA, 4, 9.6) TCA (4.3) DMSO (1.6)
Astec Chirobiotic T column, 25 cm×4.6 mm, 5 µm: isocratic mobile phase, 5° C., 20 mM ammonium acetate (pH 6.5): MeOH, 70:30
Retention times: 6PDHU (15.9, 27.5), NCBPA (7.8, 6.8)

Example 2

Isolation of a Hydantoinase from *Vigna angularis*

A protein with hydantoinase activity was isolated from *Vigna angularis* as follows:
2.1. Bean Extraction
885 g Adzuki beans (obtained from a health food store) were ground in two aliquots together with dry ice, using a conventional mixer. To the obtained bean powder 4 L extraction buffer (20 mM Tris, 10 mM ascorbic acid, 10 mM lysine, pH 7.5) was added, the suspension was stirred overnight at 4° C. filtered through gaze and centrifuged. 2500 mL crude extract with a protein content von 9.5. mg/ml were obtained and stored at –20° C. until subsequent chromatography steps (using chromatography columns from Amersham Pharmacia or GE Healthare) were performed.
2.2. Ion Exchange Chromatography (Q-Sepharose Fast Flow)
A Q-Sepharose FF-chromatography column (diameter: 5 cm; length: 21 cm) was washed with 200 mM Tris/HCl (pH 7.5), equilibrated with running buffer A (20 mM Tris/HCl, 1 mM ascorbic acid, 1 mM L-lysine*HCl, pH 7.5), and loaded with crude extract (5 g total protein). A linear gradient from running buffer A to running buffer B (20 mM Tris/HCl, 750 mM NaCl, 1 mM ascorbic acid, 1 mM L-lysine*HCl, pH 7.5) was applied and active fractions were collected.

Using the Ehrlich reagent, the activity of the fractions was determined as follows:
50 mL protein sample were incubated with 50 µL 5-hydantoin (100 mM in 100 mM borate buffer, pH 9) at room temperature for 10-60 min (depending on the enzyme content). Proteins present in the sample were completely precipitated by addition of 150 µL 12% trichloroacetic acid (TCA) and removed by centrifugation. 50 µL 4-(dimethylamino)-benzaldehyde (10% in 6 M HCl) were added to 200 µL supernate and measured photometrically at 450 nm.

2.3. Hydrophobic Chromatography (Phenyl Sepharose Fast Flow)

A phenyl sepharose column with a diameter of 5 cm and a length of 21 cm was used. The pooled active fractions of ion exchange chromatography (280 ml) were diluted to 500 ml by adding water, 67 g $(NH_4)_2SO_4$ were added to give a saturation of 25%, and the resulting mix was applied to the column. Running buffer A (20 mM Tris, 25% saturation with (NH4)2SO4, 1 mM lysine, 1 mM ascorbic acid, pH 7.5; also used as wash buffer) was applied at a flow rate of 15 mL/min. After linearly changing the column medium to running buffer B by adding two column volumes of running buffer B 20 mM Tris, 1 mM lysine, 1 mM ascorbic acid, pH 7.5), two column volumes of running buffer B were added for elution. For subsequent rinsing, buffer C (10 mM Tris/HCl, pH 7.5, 10% 2-propanol) were used. Active fractions with highest absorption as determined by a hydantoinase assay using the Ehrlich reagent were pooled.

2.4. Molecular Sieve Chromatography (Superdex Prep Grade 200 Gel Filtration)

For the next purification step a Superdex 200 column (diameter: 2.6 cm, length: 60 cm) was operated at a flow rate of 4 ml/min. To the pooled active fractions obtained from hydrophobic chromatography 70.2 g $(NH_4)_2SO_4$ were added to obtain a saturation of 80%, and the resulting mixture was centrifuged (20 min, 12.000 rpm) to obtain a pellet. The resulting pellet was dissolved in 10 mL isocratic running buffer (20 mM Tris/HCl, pH 7.5) and applied to the column.

2.5. Blue HiTrap 5 mL Affinity Chromatography

The Blue HiTrap 5 mL Affinity Chromatography column was equilibrated with buffer A (20 mM Tris/HCl, pH 7.5). After loading the pooled active fractions from molecular sieve chromatography as determined by a hydantoinase assay using the Ehrlich reagent [please confirm] the column was isocratically operated with 5 column volumes of buffer B (20 mM Tris/HCl, 500 mM NaCl, pH 7.5) and subsequently with 2 column volumes of buffer C (20 mM Tris/HCl, pH 7.5, 500 mM NaCl, 1 mM NAD, 1 mM NADP). This affinity chromatography step was used to remove glucose dehydrogenase (not showing activity with regard to glucose and NAD/NADP) by binding to the column.

2.6. Anion Exchange Chromatography (Mono Q HR 5/5)

The flow-through from the previous affinity chromatography was loaded onto a Mono Q column (diameter: 0.5 cm) at a flow rate of 1 mL/min. A linear gradient from running buffer A (20 mM Tris/HCl, pH 7.5) to running buffer B (20 mM Tris/HCl, 750 mM NaCl, pH 7.5) was applied. Pooling of the fractions was based on their respective activities and the presence of band in a protein gels.

2.7. Superose 6 Prep Grade 125 ml Gel Filtration

The pooled active fractions from the preceding anion exchange chromatography were concentrated to a volume of 1 ml (using a centriprep device with a molecular weight cutoff of 10 kD) and loaded onto a Superose column at a flow rate of 1 mL/min. As running buffer 20 mM Tris/HCl (pH 7.5) was used.

Aliquots from the various purification steps as described above were loaded onto a gel and subjected to SDS polyacrylamide electrophoresis (SDS PAGE). The resulting gel was stained with Coomassie Blue and is shown in FIG. 1, wherein the lanes from left to right correspond to:

1) Molecular Weight Standard (Precision Plus Protein Marker from BioRad, corresponding to 10, 15, 20, 25, 37, 50 75, 100, 150 and 250 kD, respectively)
2) Cell free extract before purification
3) Q-Sepharose FF anion exchange fraction
4) Phenylsepharose FF HIC fraction
5) Superdex Prep Grade 200 Gel Filtration fraction
6) Blue HiTrap 5 ml Affinitats-Chromatography fraction
7) Mono Q HR 5/5 anion exchange fraction
8) Superose 6 prep grade 125 ml Gel Filtration fraction
9) Molecular Weight Standard (as in Lane 1)
10) Independent preparation (corresponding to a Mono Q HR anion exchange fraction)

A partially purified protein with a molecular weight of approximately 55 kD with was obtained (indicated by the upper arrow in FIG. 1). The second protein of approximately 35 kD (indicated by the lower arrow in FIG. 1) is glucose dehydrogenase.

Pooled fractions from Superose 6 prep grade gel filtration were precipitated with chloroform/methanol, and 500 µL formic acid (70%) were added to the precipitate. 1-2 BrCN crystals were added in order to effect bromo cyan cleavage. A solution of bovine serum albumin (BSA, 2 mg/ml) was used as cleavage control. After incubating both solution for 2-3 hours at room temperature, formic acid and bromo cyan were removed by a nitrogen flow. The residues were dissolved in a tricin gel sample buffer containing 1% mercaptoethanol and incubated 5 min at 95° C. The obtained samples were loaded onto a tricin gel (10-20% gradient) and blotted onto a PVDF membrane. The peptide fragments on the blot were identified by staining and subjected to N-terminal sequencing.

The following potential peptide sequences were identified:

```
IELGITGPEGQRLAGPTVL      (SEQ ID NO: 1)

IELGITGPEGQRLAGPVL       (SEQ ID NO: 2)

IELITGPEGQRLAGPTVL       (SEQ ID NO: 3)

IELITGPEGQRLAGPVL        (SEQ ID NO: 4)

EEIARARKSGQRVIGEPVAS     (SEQ ID NO: 5)

ITGPEGQRLAGP             (SEQ ID NO: 7)
```

The obtained partial sequences have a high homology to a sequence from *Glycine max* with the Genbank accession number ACU20291 (SEQ ID NO:6), which is referred to a D-hydantoinase, thus confirming the hydantoinase nature of the isolated protein. SEQ ID NO:6 is shown below, the regions of homology are underlined:

```
mqfsitsqflhifsltifiiitsslsqssqfcdagteipsskllikggtvvnaqhhqia dvyvedgiivavnpnimvgddvtvidatgkyvmpggidphthldmdvgftatvddffsgqaaal aggttmhidfvipingsltagfedyekkakkscmdygfhmvitkwdetvsremelmvkekgins fkffmaykgilmindellegfkkckslgavamvhaengdavyegqrkmielgitgpeghalsr
``` pavlegeataralrladfvntplyvvhvmsidam<u>eeiakarkagqrvigepias</u>glaldeswlw hpdfeiaakyvmsppirkrghdkalqaalstgvlqlvgtdhcafnstqkargiddfrkmpngvn gieermhlvwdimvesgqisvtdyvritstecakifniyprkgavlpgsdadiiilnpnssfem sakshhsrldtnvyegrrgkgkievtiaggrvvwennelkvtpgtgryiqmppfsylfdgldkk daiylnslqapvkrakas

Example 3

Activity Comparison Between Commercially Available Hyandantoinase and Isolated Hydantoinase The activities of hydantoinase obtained from Sigma and hydantoinase isolated in Example 2 were compared.

To determine and compare the specific activity of the Sigma enzyme and the purified hydantoinase (BP) 5 mM of hydantoin, 5-phenylhydantoin or 6-phenyldihydrouracil, respectively, in 50 mM Tris HCl pH 7.5 were incubated with different amounts of enzyme for 30 min at 40° C.

The reaction was stopped by adding conc. HCl and then measured by HPLC.

The following Table 1 is showing the specific activities from the sigma enzyme and the enzyme isolated in Example 2. Both enzymes show the highest activity towards 5-phenylhydantoin followed by hydantoin.

TABLE 1

| Substrate | Enzyme from Sigma | Enzyme from Example 2 |
|---|---|---|
| Hydantoin | 217 | 425 |
| 5-Phenylhydantoin | 261 | 557 |
| 6-Phenyldihydrouracil | 6 | 72 |

Example 4

Synthesis of Racemic 6-Substituted Dihydrouracils (General Scheme)

Figure 2:
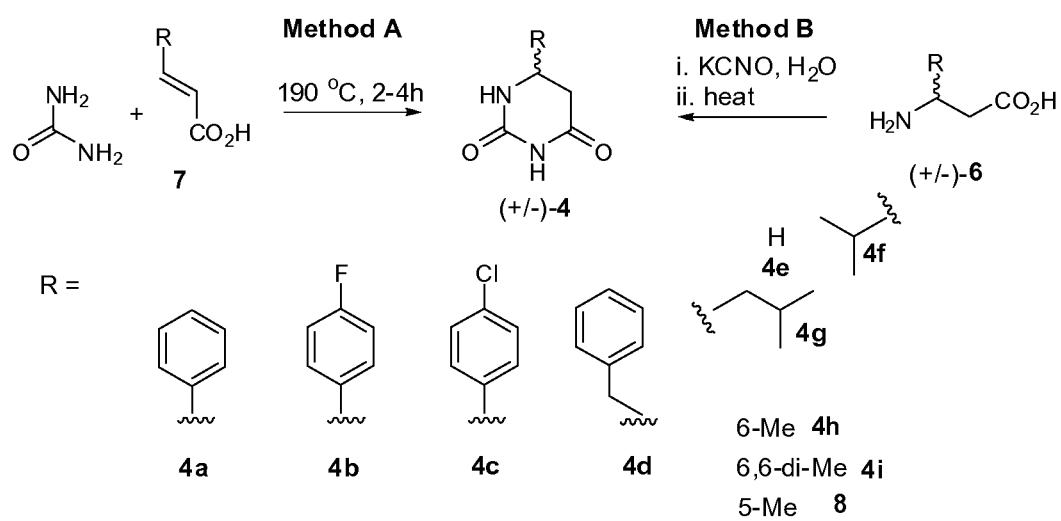
FIG. 2 shows two exemplary ways for synthesizing racemic 6-substituted dihydrouracils.

The required 6-substituted dihydrouracil substrates 4a-i were prepared by one of two alternative routes (FIG. 2). In method A (Cabaleiro, M. C., Journal of Chemical Research 7:318-320, 2000), urea was heated with the appropriate cinnamic acid derivative 7 at 190° C. for 2-4-h, followed by recrystallisation of the product, to yield 4a-i in ~45% yield. Method B involved treatment of the corresponding racemic β-amino acid with potassium cyanate followed by heating to effect cyclisation to give 4a-i in high yield. Method B, which is known to proceed without racemisation, was also used to prepare enantiomerically pure (S)-4a and (S)-5a, by using enantiomerically pure (S)-6a as the starting material.

Example 5

Synthesis of Racemic 6-Substituted Dihydrouracils or Precursor Molecules (Individual Syntheses)

a) Synthesis of (±)-6-phenyldihydrouracil according to the following formula

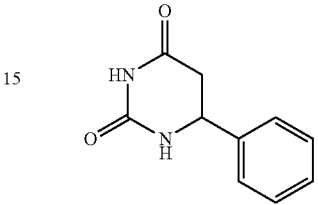

A mixture of trans-cinnamic acid (10.00 g, 67.5 mmol) and urea (20.25 g, 337.5 mmol) was heated to 210° C. over 30 minutes. This resulted in the formation of a homogenous yellow liquid. For each hour that the reaction proceeded additional urea (2.03 g, 33.8 mmol) was added. After stirring for 4 hours, boiling water (80 mL) was added and the reaction mixture was allowed to stir for a further 1 hour at 95° C. After removal of the residual solid from the reaction mixture by hot filtration, the white precipitate which formed was isolated by filtration, to afford a white solid (6.0 g, yield=46%). $R_f$ 0.3 (EtOAc); $\delta_H$ (400 MHz, DMSO-$d_6$) 2.61 (1H, dd, J=6.8, 16.1, $CH_2$), 2.83 (1H, dd, J=5.8, 16.1, $CH_2$), 4.64-4.70 (1H, m, CHPh), 7.27-7.41 (5H, m, Ph), 8.01 (1H, bs, CHNHCO), 10.18 (1H, br. s, CONHCO); $\delta_C$ (100 MHz, DEPT, DMSO-$d_6$) 38.6 ($CH_2$), 50.4 (CHPh), 126.4 (Ph), 128.0 (Ph), 129.0 (Ph), 141.5 (CPh), 154.2 (NHCONH), 170.2 (NHCOCH2); $R_t$ 9.6 and 14.8 minutes (chirobiotic T, ammonium acetate buffer pH 5.5:methanol 7:3, 1 mL/minute).

b) Synthesis of methyl trans-cinnamate according to the following formula:

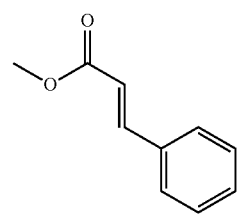

To a solution of trans-cinnamic acid (500 mg, 3.4 mmol) in methanol (5 mL) was added concentrated sulphuric acid (100 µL). After 10 minutes irradiation by microwave (300 W, 200° C.) the solvent removed in vacuo. The white solid precipitate was dissolved in ethyl acetate (10 mL) and the organic layer washed with twice with sodium hydrogen carbonate (5 mL) and brine (5 mL) before the solvent removed in vacuo to afford the white crystalline solid (468 mg, 86%). δ$_H$ (400 MHz, DMSO-d$_6$) 3.73 (3H, s, CH$_3$), 6.65 (1H, d, J=16.1, CHCHPh), 7.40-7.46 (3H, m, Ph), 7.67 (2H, d, J=16.1, CHCHPh), 7.70-7.76 (2H, m, Ph).

c) Synthesis of hydrocinnamoyl fluoride according to the following formula:

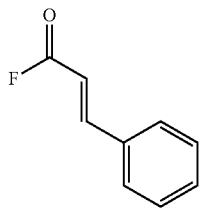

To a stirred room temperature solution of trans-cinnamic acid (500 mg, 3.4 mmol) in anhydrous DCM (5 ml) under N2 atmosphere was added dimethylaminosulfur trifluoride (0.31 ml, 2.4 mmol). After stirring for 2 hours ice-cold water (5 ml) was added. The organic layer was separated and the aqueous layer extracted with DCM (5 ml). The combined DCM layers were washed twice with ice-cold water (5 ml), dried (MgSO4) and the solvent removed in vacuo to afford a brown oil (451 mg, 88%) which was used in subsequent reactions without further purification. δ$_H$ (400 MHz, DMSO-d$_6$): 6.78 (1H, dd, J=8.0, 16.1 CHC(O)F), 7.45-7.55 (3H, m Ph), 7.81-7.86 (1H, m, Ph), 7.97 (1H, d, J=16.0, CHPh). 50 (100 MHz, DEPT, DMSO-d$_6$) 112.6 (CHCHPc), 129.4 (Ph), 129.6 (Ph), 132.3 (Ph), 133.5 (Ph), 152.2 (CHPh), 159.1 (C(O)F).

d) Synthesis of (±)-3-fluoro-6-phenyldihydrouracil according to the following formula:

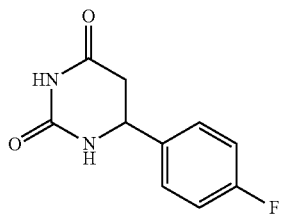 [SMILES: O=C1CC(c2ccc(F)cc2)NC(=O)N1]

A mixture of para-fluoro-trans-cinnamic acid (1.00 g, 6.67 mmol) and urea (2.00 g, 33.5 mmol) was heated to 210° C. over 30 minutes. This resulted in the formation of a homogenous yellow liquid. For each hour that the reaction proceeded additional urea (0.40 g, 6.67 mmol) was added. After stirring for 4 hours, boiling water (20 mL) was added and the reaction mixture was allowed to stir for a further 1 hour at 95° C. After removal of residual solid from the reaction mixture by hot filtration, the white precipitate which formed was isolated by filtration, to afford a yellow solid (0.75 g, yield=60%). SH (400 MHz, DMSO-d$_6$) 2.61 (1H, dd, J=6.8, 16.4, CH$_2$), 2.84 (1H, dd, J=5.8, 16.4, CH$_2$), 4.64-4.70 (1H, m, CHPh), 7.27-7.42 (4H, m, Ph), 8.02 (1H, bs, CHNHCO), 10.19 (1H, br. s, CONHCO); δ$_C$ (100 MHz, DEPT, DMSO-d$_6$) 38.2 (CH$_2$), 50.0 (CHPh), 126.0 (Ph), 127.6 (Ph), 128.5 (Ph), 141.1 (Ph), 153.8 (NHCONH), 169.7 (NHCOCH$_2$); R$_1$ 10.5 and 15.1 minutes (chirobiotic T, ammonium acetate buffer pH 5.5:methanol 7:3, 1.0 mL/minute).

e) Synthesis of (±)-3-bromo-6-phenyldihydrouracil according to the following formula:

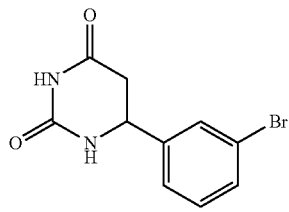 [SMILES: O=C1CC(c2cccc(Br)c2)NC(=O)N1]

A mixture of meta-bromo-trans-cinnamic acid (0.80 g, 3.5 mmol) and urea (1.26 g, 21 mmol) was heated to 210° C. This resulted in the formation of a homogenous yellow liquid. Additional urea (0.25 g, 4.2 mmol) was added for each hour that the reaction proceeded. After stirring for four hours, boiling water (20 mL) was added and the reaction mixture was allowed to stir for a further 1 hour at 95° C. After removal of residual solid from the reaction mixture by hot filtration, the white precipitate which formed was isolated by filtration, to afford a yellow solid (0.30 g, yield=32%). δ$_H$ (400 MHz, DMSO-d$_6$) 2.66 (1H, dd, J=6.8, 17.4, CH$_2$), 2.84 (1H, dd, J=5.6, 16.3, CH$_2$), 4.64-4.74 (1H, m, CHPh), 7.29-7.59 (4H, m, Ph), 8.04 (1H, br. s, CHNHCO), 10.23 (1H, br. s, CONHCO); δ$_C$ (100 MHz, DEPT, DMSO-d$_6$) 37.8 (CH2), 49.5 (CHPh), 121.1 (Ph), 125.2 (Ph), 129.0 (Ph), 130.5 (Ph), 130.8 (Ph), 143.9 (Ph), 153.7 (NHCONH), 169.6 (NHCOCH2); R$_1$ 16.3 and 25.1 minutes (chirobiotic T, ammonium acetate buffer pH 5.5:methanol 7:3, 1.0 mL/minute).

f) Synthesis of (±)—N-carbamoyl-β-phenylalanine

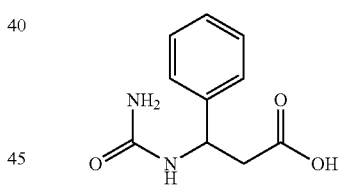

To a stirred solution of (±)-β-phenylalanine (0.80 g, 4.85 mmol) in hot water (20 mL) was added a solution of potassium cyanate (0.60 g, 7.40 mmol) in water (2 mL). After stirring for 1 hour at 90° C., the reaction mixture was allowed to cool to room temperature before it was acidified using concentrated hydrochloric acid (pH>1). Upon standing a white precipitate formed, which was isolated by filtration and recrystallised from boiling water to afford a white crystalline solid (0.71 g, 71%). δ$_H$ (400 MHz, DMSO-d$_6$) 2.63 (2H, CH$_2$CO$_2$H), 5.00 (1H, dd, J=7.2, 8.7, CHNH), 5.56 (2H, s, NH$_2$), 6.57 (1H, d, 8.7, CHNH), 7.18-7.34 (5H, m, Ph); 50 (100 MHz, DEPT, DMSO-d$_6$) 41.4 (CH$_2$), 50.0 (CHPh), 126.3 (Ph), 126.7 (Ph), 128.1 (Ph), 143.4 (Ph), 157.8 (NHCONH), 172.0 (NHCOCH2); Rt 3.1 and 3.4 minutes (chirobiotic T, ammonium acetate buffer pH 5.5:methanol 7:3, 1.0 mL/minute).

g) Synthesis of (R)—N-carbamoyl-β-phenylalanine according to the following formula:

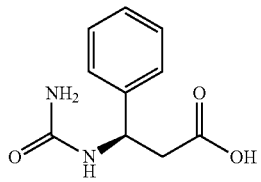 [SMILES: NC(=O)N[C@H](CC(=O)O)c1ccccc1]

To a stirred solution of (R)-β-phenylalanine (0.4 g, 2.43 mmol) in hot water (10 mL) was added a solution of potassium cyanate (0.3 g, 3.70 mmol) in water (1 mL). After stirring for 1 hour at 90° C., the reaction mixture was allowed to cool to room temperature before it was acidified using concentrated hydrochloric acid (pH>1). Upon standing a white precipitate formed, which was isolated by filtration and recrystallised from boiling water to afford a white crystalline solid (0.30 g, 60%); $\delta_H$ and $\delta_C$ analysis identical to (±)-46; $R_t$ 3.4 minutes (chirobiotic T, ammonium acetate buffer pH 5.5: methanol 7:3, 1.0 mL/minute).

h) Synthesis of (±)-6-phenyldihydrouracil (according to the subsequent formula) from (±)—N-carbamoyl-β-phenylalanine

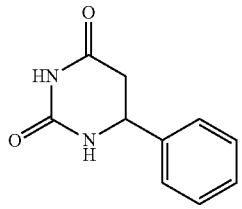 [SMILES: O=C1CC(c2ccccc2)NC(=O)N1]

A solution of (±)—N-carbamoyl-β-phenylalanine (100 mg, 0.48 mmol) in concentrated hydrochloric acid (5 mL) was stirred for 4 hours at 135° C. After that period the volume of reaction mixture had reduced by 75%, and the reaction mixture was allowed to cool to room temperature. Upon standing a white precipitate formed, which was isolated by filtration to afford a white crystalline solid (50 mg, 55%); analysis identical to (±)-45.

i) Synthesis of (S)-6-phenyldihydrouracil according to the following formula:

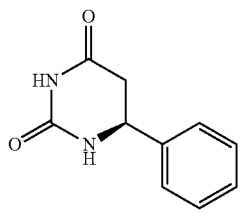 [SMILES: O=C1C[C@@H](c2ccccc2)NC(=O)N1]

To a stirred solution of (S)-β-phenylalanine (100 mg, 0.60 mmol) in hot water (2 mL) was added a solution of potassium cyanate (75 mg, 0.93 mmol) in water (0.5 mL). After stirring for 1 h at 90° C., concentrated hydrochloric acid (2 mL) was added the reaction was stirred for 2 h at 135° C. After which time the volume of mixture had reduced by 75%, and it was allowed to cool to room temperature. Upon standing a white precipitate formed, which was isolated by filtration to afford a white crystalline solid (55 mg, 48%); $\delta_H$ and $\delta_C$ analysis identical to (±)-45; $R_t$ 9.6 minutes (chirobiotic T, ammonium acetate buffer pH 5.5:methanol 7:3, 1 mL/minute).

Example 6

Isolation of Educt and Product of a Hydantoinase Reaction

The binding of 6-PDHU and NCBPA to Q Sepharose and DEAE Sepharose was tested in microcaps (Eppendorf). 1 mL of Q Sepharose or DEAE Sepharose (commercially available suspension in ethanol) was washed with water (3×1 mL) before a solution (1 mL) containing 2.5 mM NCBPA and 2.5 mM 6-PDHU was added, the microcap was vortexed before an aliquot of the supernatant was removed. The percentage of NCBPA and 6PDHU in the supernatant were determined by rpHPLC and are shown in Table 2:

TABLE 2

| Resin Type | Percent in supernatant (%) | |
|---|---|---|
| | NCBPA | 6PDHU |
| Q | 38 | 58 |
| DEAE | 22 | 67 |

Binding on both resins is rapid, with Q binding less N-carbamoyl-β-phenylalanine and more 6-pheyldihydrouracil than DEAE, making DEAE more favourable an anion exchange resin for the separation.

Example 7

Chiral Reverse Phase HPLC

For chiral rpHPLC the following column, buffer and running conditions were used:
Astec Chirobiotic™ T 25 cm×4.6 mm, 5 μm (Sigma-Aldrich, St. Louis, USA) Ammonium Acetate buffer (pH 5.5):Methanol, 70:30, 25° C., 0.5 mL/min Example 8

Separation of Enzyme, Substrate and Product by DEAE Chromatography

Figure 3:
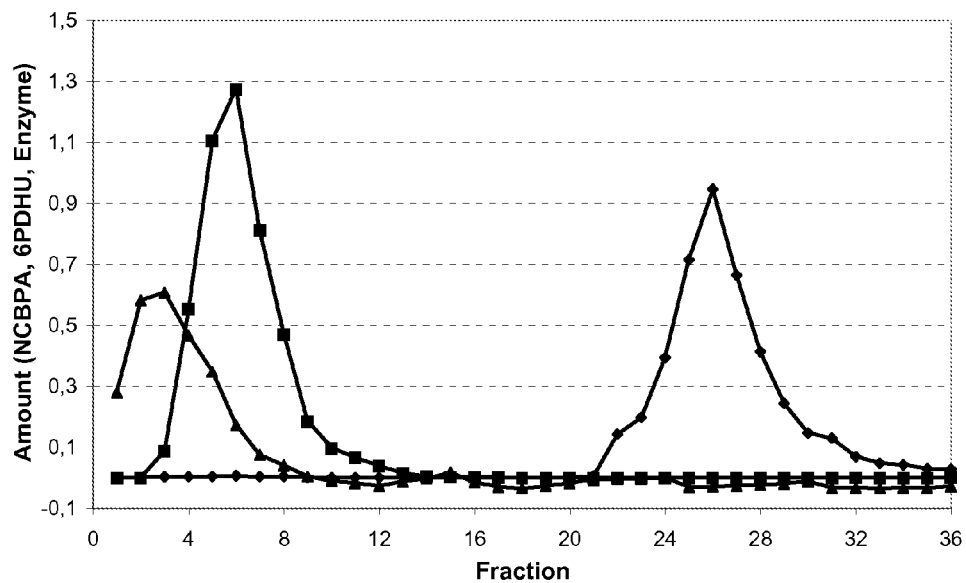
FIG. 3 shows the separation of N-carbamoyl-β-phenylalanine (NCBPA), 6-phenyldihydrouracil (6-PDHU) and enzyme by anion exchange chromatography (DEAE column).

A column was prepared from an inverted syringe, blocked with glass wool and filled with DEAE (4 mL) that had been washed with 10 column volumes of $dH_2O$. After equilibration with 200 mM ammonium acetate buffer (pH 4) a synthetic mixture of NCBPA (2.5 mM), 6PDHU (2.5 mM) and enzyme (7 mg/mL) in $H_2O$ was applied to the column and the flow through was analysed by rpHPLC (6PDHU/NCBPA detection) and Bradford assay (enzyme detection). After all 6PDHU had been washed from the column, NCBPA was eluted from the column using 200 mM ammonium acetate (pH 8.17). The results are shown in FIG. 3 (wherein squares represent 6-PDHU; diamonds represent NCBPA, and triangles represent enzyme, 6-PDHU and NCBPA are indicated in mM, enzyme is indicated in mg/L). At a pH of 4 there is a clear separation between NCBPA and 6PDHU, allowing the recovery of 90% of NCBPA.

Example 9

Hydantoinase Catalysed Hydrolysis of Racemic 6-Substituted Dihydrouracils

Figure 4:
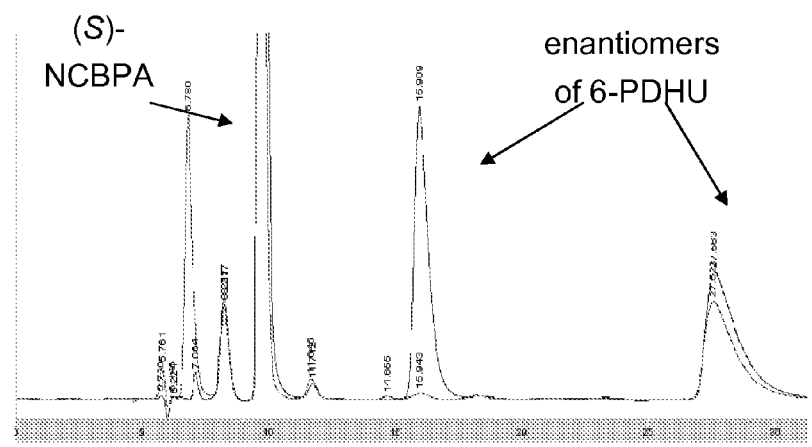
FIG. 4. shows the results of a reverse phase chiral HPLC after hydantoinase catalysed hydrolysis of 6-PDHU.
Figure 5:
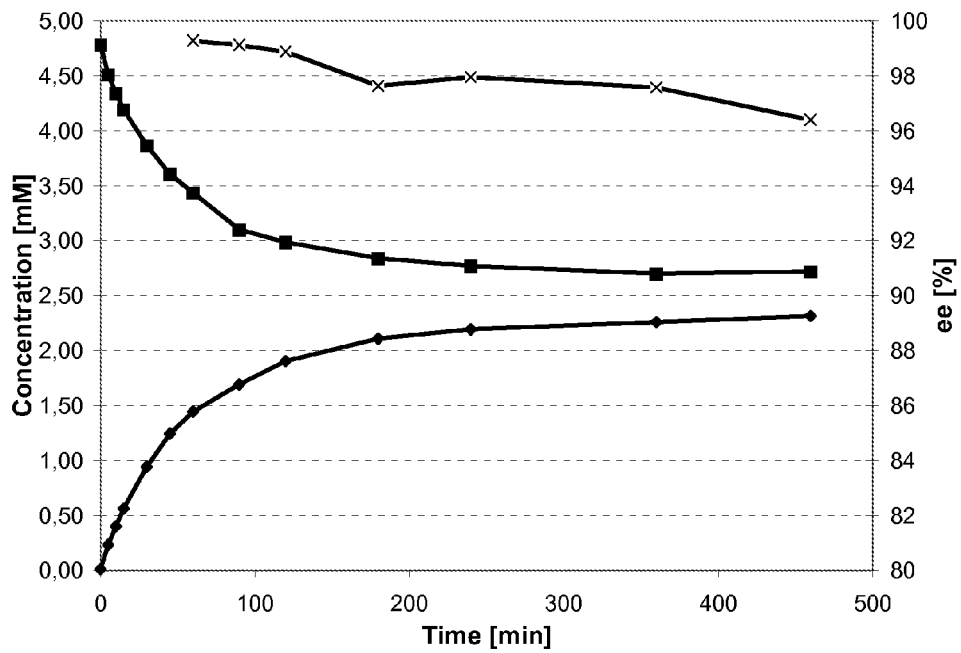
FIG. 5 shows the conversion rates over time of 6-PDHU into N-carbamoyl derivative (NCBPA) and the respective enantiomeric excess rates.
Figure 6:
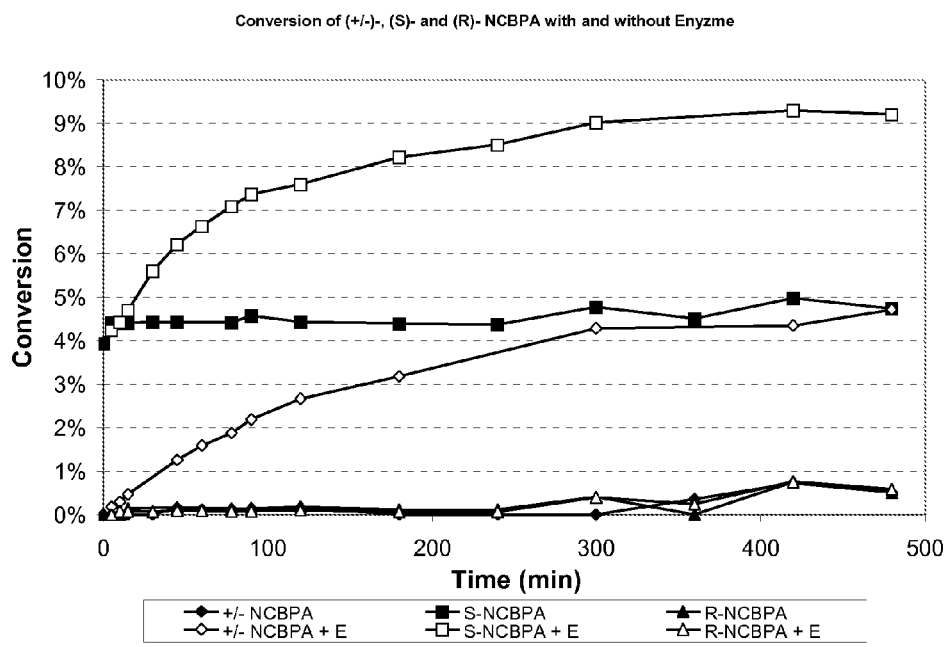
FIG. 6 shows the cyclisation of N-carbamoyl-β-phenylalanine in the absence or presence of hydantoinase.

Initially the hydantoinase (obtained form Sigma, St. Louis, USA) catalysed hydrolysis of (±)-6-PDHU (racemic 6-phenyldihydrouracil) (4a in FIG. 2: R=Ph) was studied as a model system. Reactions were carried out at a substrate concentration of 5 mM in Tris buffer [pH 7.5] and monitored by reverse-phase chiral HPLC as described in Example 7, which allowed simultaneous determination of both the extent of conversion in the reaction and also the enantiomeric excess of unreacted dihydrouracil 4a and the N-carbamoyl derivative 5 (FIG. 4, cf. also Scheme 2). The following observations were noted:
(i) the hydantoinase enzyme was found to be highly selective for the (S)-enantiomer of 6-PDHU (4a) with an E value>100. The absolute configuration of both the product (S)-N-carbamoyl-β-pheynylalanine [(S)-NCBPA] and unreacted substrate (R)-6-DPHU were assigned by comparison with authentic samples;
(ii) despite the high (S)-enantioselectivity observed, conversions did not proceed to 50%, even after prolonged reaction times. All reactions gave an equilibrium concentration of 6-PDHU:(S)-NCBPA=51:49. The enantiomeric excess of (S)-NCBPA exceeded 96% during the whole observation period. FIG. 5 shows the results obtained from a 25 mL-reaction in a small reactor, wherein diamonds represent the concentration of NCBPA [mM], squares represent the concentration of 6-DPHU [mM], and crosses represent the enantiomeric excess [%]
(iii) the reverse reaction, namely cyclisation of N-carbamoyl-β-phenylalanine, was found to have an appreciable rate relative to hydrolysis and was also highly (S)-selective with no appreciable cyclisation of the (R)-enantiomer. FIG. 6 shows the conversion of (+/−)-, (S)- and (R)-NCBPA with and without enzyme, wherein closed or open diamonds connected by solid lines represent+/−NCBPA (without enzyme) or +/−NCBPA (with enzyme), respectively, closed or open squares connected by solid lines represent (S)-NCBPA (without enzyme) or (S)-NCBPA (with enzyme), respectively, and closed or open triangles connected by solid lines represent (R)-NCBPA (without enzyme) or (R)-NCBPA (with enzyme), respectively.

Example 10 pH Dependency of Chemical Hydrolysis of 6-PDHU

Figure 7:
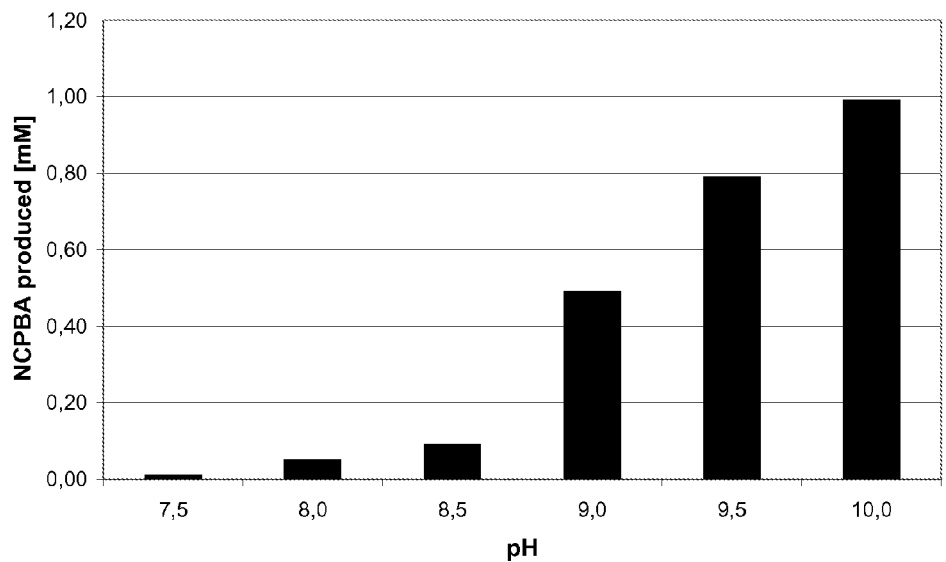
FIG. 7 shows the pH dependency of chemical hydrolysis of 6-DPHU in Tris buffer devoid of hydantoinase.

6-PDHU was incubated at 50° C. for 24 hours in Tris buffer at different pH values. Appreciable background hydrolysis of 6-PDHU occurred with a strong pH and buffer dependency. In Tris buffer at pH 7, a background hydrolysis of 0.5% was observed. At pH 9, the background hydrolysis amounted to ca. 20% (FIG. 7).

Example 11 pH Dependency of Hydantoinase Activity

Figure 8:
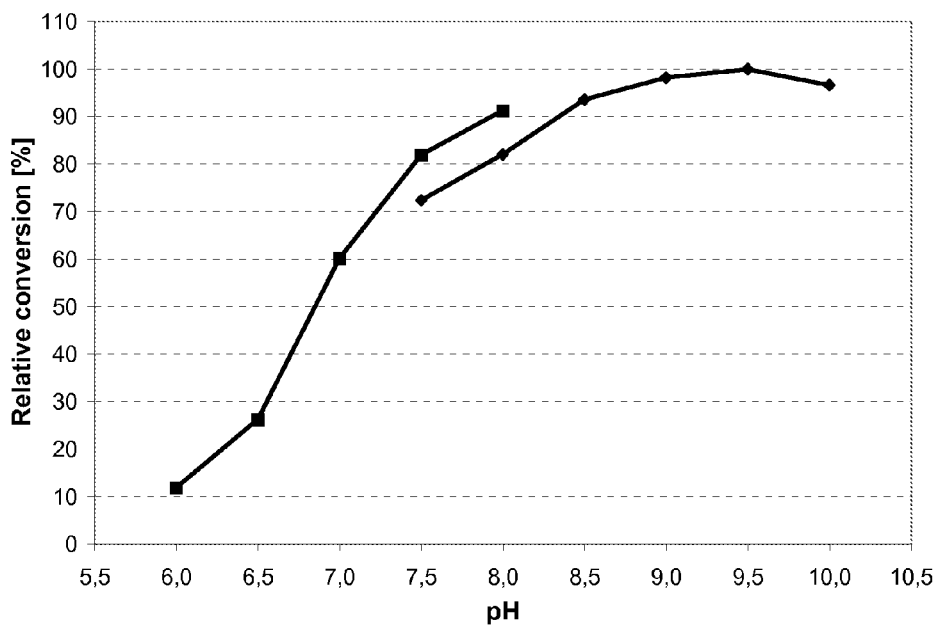
FIG. 8 shows the pH dependency of hydantoinase mediated enzymatic conversion of 6-DPHU.

6-PDHU was incubated in phosphate buffer (0.1 M, potassium dihydrogen phosphate and dipotassium hydrogen phosphate, volumes adjusted to the appropriate pH) or Tris buffer at various pH values for (up to 8h, using 7 g/L D-hydantoinase from Sigma). The highest rate of conversion was observed in the range from about pH 7.5 and about pH 9.0 (FIG. 8, wherein squares represent phosphate buffer and diamonds represent Tris buffer).

Figure 9:
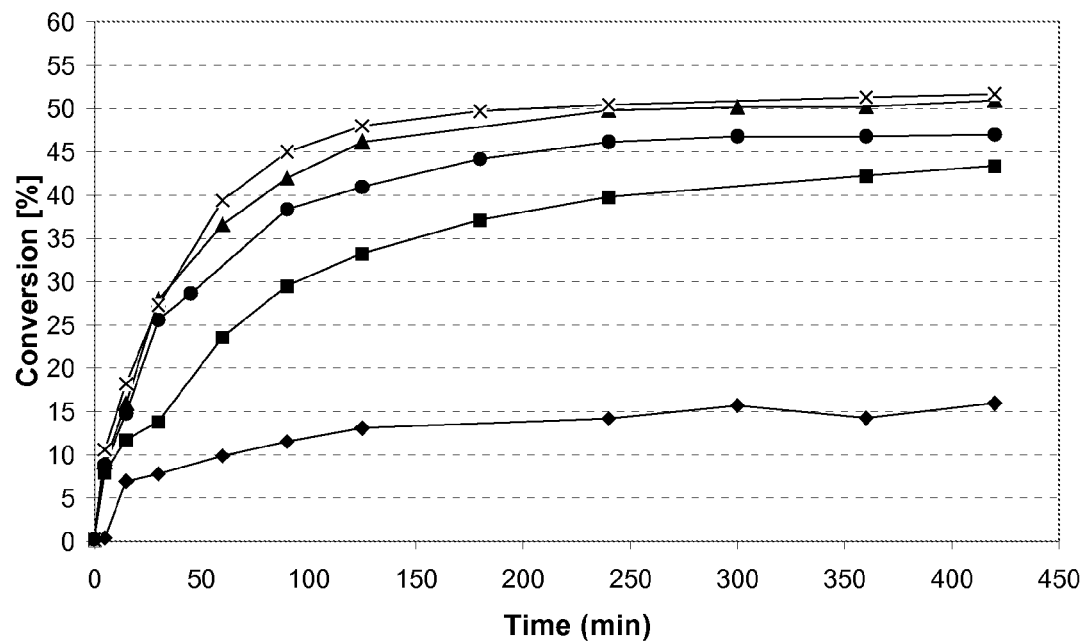
FIG. 9 shows the conversion rates of hydantoinase in different pH value/buffer combinations over time.

In an additional experiment conversion rates were determined for phosphate or Tris buffers at various pH values over time. 5 mM 6-PHDU was incubated in phosphate buffer (pH 6.0, 7.0, 7.5, 8.0) and Tris buffer (pH 7.5) buffers for 22 hours. The results are shown in FIG. 9 (wherein diamonds, squares, triangles and crosses represent phosphate buffer at pH 6, pH 7, pH 7.5 or pH 8, respectively, and dots represents Tris buffer at pH 7.5) and Table 3 (ee=enantiomeric excess [%]).

TABLE 3

| Buffer | pH | ee |
|---|---|---|
| Phosphate | 6.00 | >99.90 |
| Phosphate | 7.00 | >99.90 |
| Phosphate | 7.50 | 96.62 |
| Phosphate | 8.00 | 92.73 |
| Tris | 7.50 | >99.90 |

While the conversion proceeds with high enantiomeric excess of the desired substrate at pH 6.00 in phosphate buffer, the conversion rate is considerably lower compared to the conversion rates at pH values between 7.00 and 8.00.

Example 12

Substrate Specificity of *Vigna angularis* Hydantoinase

Figure 10:
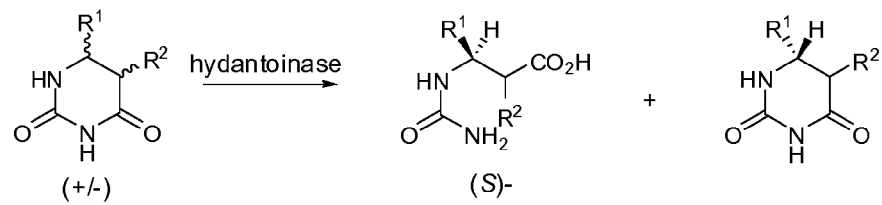
FIG. 10 shows the reaction catalyzed by D-hydantoinase from *Vigna angularis* (Sigma).

Various substrates were synthesized as described in Example 4 and subjected to hydantoinase catalyzed conversion [Tris buffer (pH 7.5, 0.1 M, 1.0 mL), D-hydantoinase, (Sigma, 7 g/L), substrate (5 mM solutions predissolved in buffer unless aromatic substituent (4a, 4b, 4c), in which case substrate is dissolved in 100 microlitres DMSO and added to 900 microlitres of buffer)]. The reaction is shown in FIG. 10, the results are shown in Table 4, wherein the E-value is defined as follows:

$$E\text{ value} = (\ln(1-[\text{product}](1+ee)))/(\ln(1-[\text{product}]*(1-ee)))$$

TABLE 4

| Substrate | $R^1$ | $R^2$ | Method synthesis | Yield NCBAA/% | Yield DHU/% | Relative rate of enzymatic hydrolysis | E value |
|---|---|---|---|---|---|---|---|
| 4a | $C_6H_5$ | H | A & B | 88 | 77-82 | 7 | >200 |
| 4b | p-F—$C_6H_4$ | H | B | 56 | 67 | 15 | >100 |
| 4c | p-Cl—$C_6H_4$ | H | B | 71 | 75 | 41 | >100 |
| 4d | Benzyl | H | B | 87 | 58 | 79 | 0 |
| 4e | H | H | B | 55 | — | 100 | — |
| 4f | i-Pr | H | B | 80 | 24 | 46 | 3 |
| 4g | i-Bu | H | B | 68 | 67 | 55 | 2 |
| 4h | Me | H | — | — | — | 52 | 5 |
| 4i | (Me)$_2$ | H | B | 20 | 100 | 0 | — |
| 8 | H | Me | — | — | — | 23 | — |

Example 13

Influence of Organic Co-Solvents of Hydantoinase-Catalysed Conversion

Figure 11:
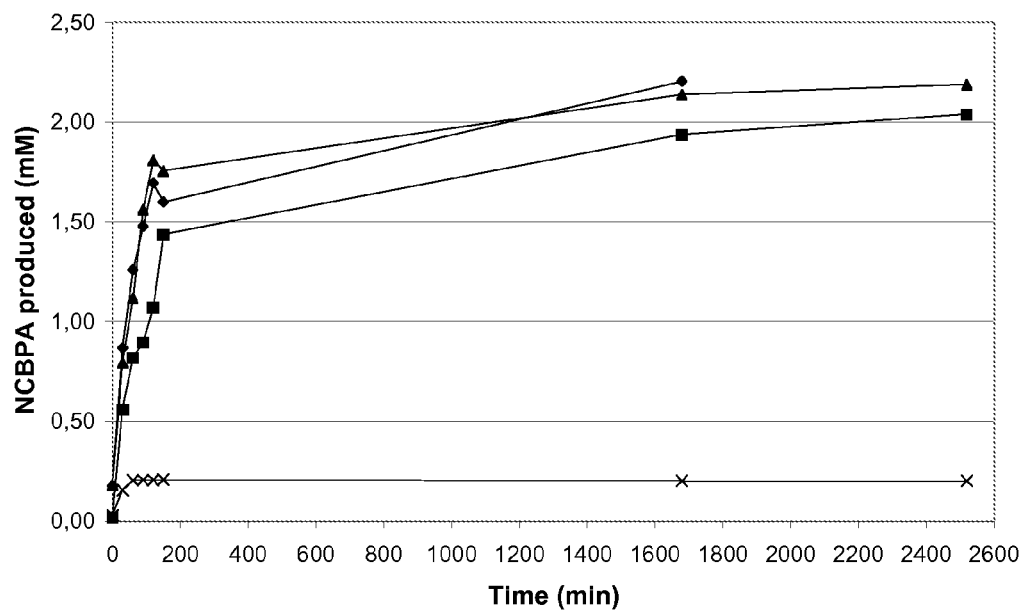
FIG. 11 shows the influence of organic co-solvents on hydantoinase-catalyzed conversion of 6-PDHU.

Biotransformations of 5 mM 6-PDHU were carried out in a 5 mL-scale in buffer with 2% DMSO and buffer that had been saturated with either MTBE (approximately 5 vol.-%) or butan-2-ol (approximately 15 vol.-%). The results are shown in FIG. 11, wherein diamonds represent buffer, squares represent buffer containing 2% DMSO, triangles represent buffer containing MTBE, and crosses represent buffer containing butane-2-ol. Neither DMSO nor MTBE considerably affected the conversion while butane-2-ol reduced the amount of NCBPA at the concentration used.

Example 14

Influence of Enzyme Amount on Conversion and Enantiomeric Excess

Figure 12:
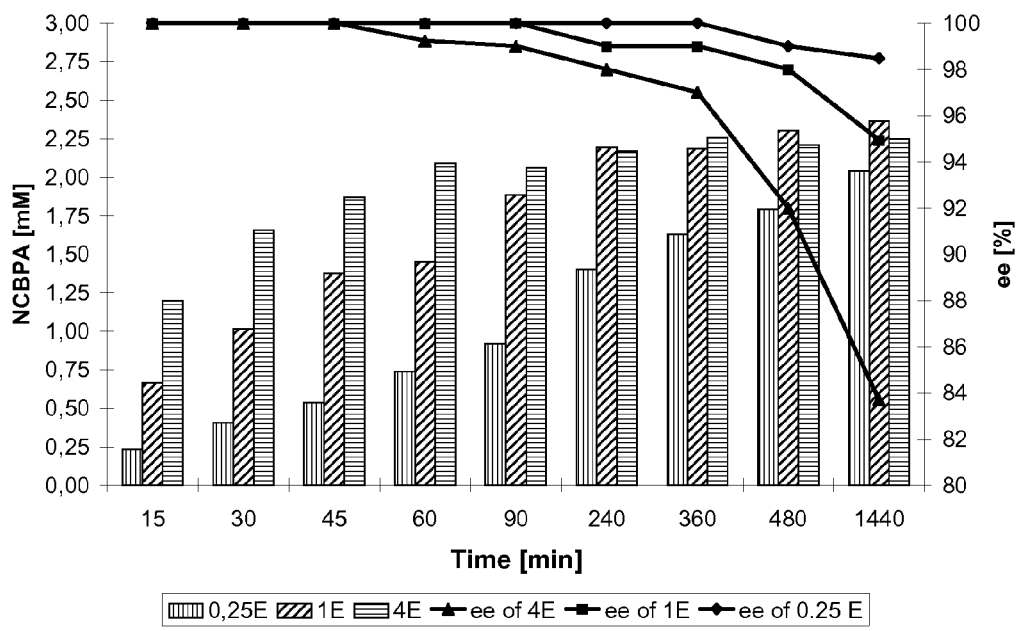
FIG. 12 shows the influence of different hydantoinase concentrations on product formation and enantiomeric excess.

Three parallel reaction setups were performed in a total reaction volume of 5 mL Tris buffer, pH 7.5 each, containing 5 mM 6-PDHU, a temperature of 50° C. In one reaction the usual amount of enzyme (7 g/L) was used, while the other setups contained 0.25 equivalents (1.75 g/L) and 4 equivalents (28 g/L), respectively. The production of N-carbamoyl-β-phenylalanine (NCBPA) and the enantiomeric excess of the S-enantiomer were determined at various time points. The results are shown in FIG. 12, wherein vertically, obliquely or horizontally hatched columns represent the concentration of NCBPA obtained in the presence of 0.25, 1 or 4 equivalents of enzyme, respectively, and wherein diamonds, squares and triangles represent the corresponding enantiomeric excess in the presence of 0.25, 1 or 4 equivalents of enzyme, respectively.

Example 15

Upscaling of a Hydantoinase-Catalysed Reaction

Figure 13:
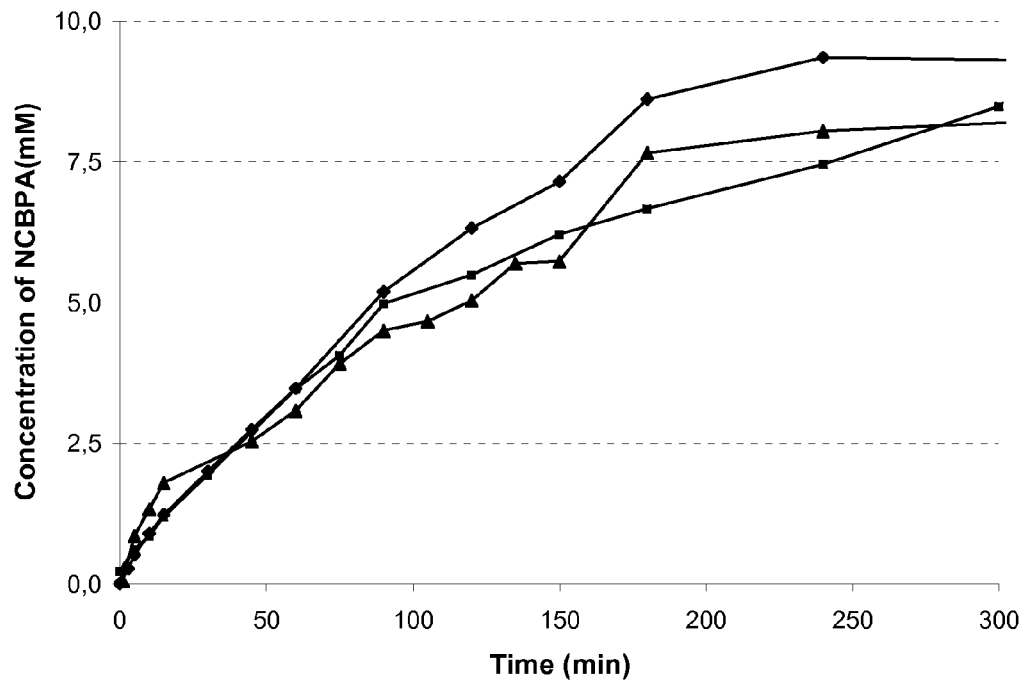
FIG. 13 shows the production of NCBPA in 25 mL reactions.
Figure 14:
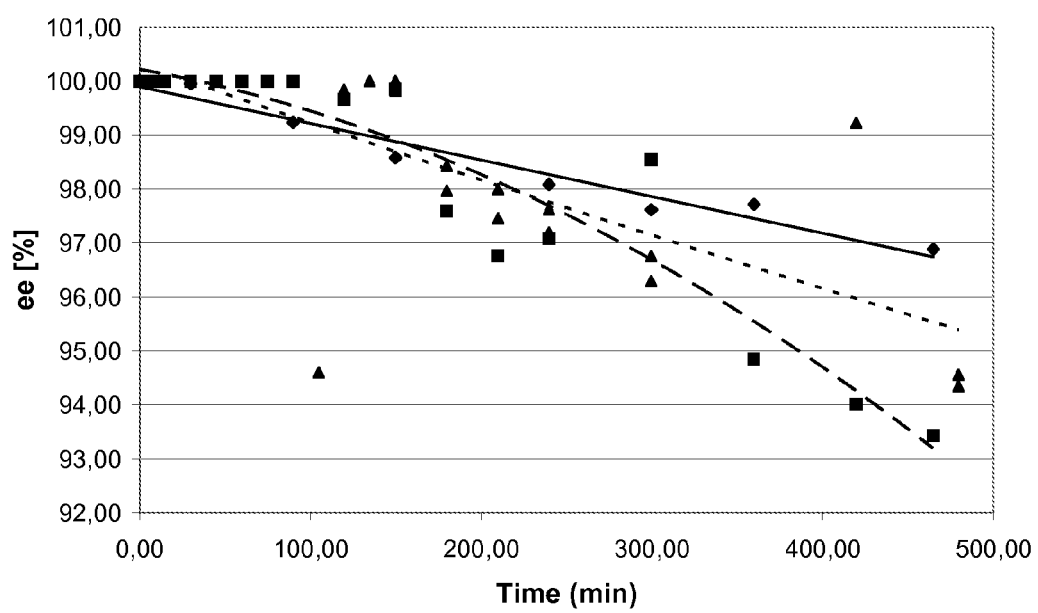
FIG. 14 shows the enantiomeric excess of S-NCBPA in 25 mL reactions.

In three independently performed biotransformations 20 mM 6-PDHU were incubated at 50° C. in a total reaction volume of 25 ml buffer (Tris buffer pH 7.5) and in the presence of 175 mg hydantoinase. The pH of the buffer was adjusted upon addition of 6-PDHU and kept constant during the course of the reaction by automatic titration of NaOH. Aliquots were taken at various time points for determining the concentrations of NCBPA and the enantiomeric excess of the S-enantiomer. The results are shown in FIG. 13 and FIG. 14, respectively. In FIG. 13 diamonds, squares and triangles represent reactor run 1, reactor run 2 and reactor run 3, respectively. In FIG. 14 diamonds, squares and triangles represent the enantiomeric excess rates observed in reactor run 1, reactor run 2 and reactor run 3, respectively, and wherein solid, dashed and dotted lines represent the best fit curves of the enantiomeric excess rates observed in reactor run 1, reactor run 2 and reactor run 3, respectively.

Summary of SEQ ID NOs:
SEQ ID NO:1—peptide sequence obtained from isolated hydantoinase
SEQ ID NO:2—peptide sequence obtained from isolated hydantoinase
SEQ ID NO:3—peptide sequence obtained from isolated hydantoinase
SEQ ID NO:4—peptide sequence obtained from isolated hydantoinase
SEQ ID NO:5—peptide sequence obtained from isolated hydantoinase
SEQ ID NO:6—hydantoinase from *Glycine max* as sequence reference
SEQ ID NO:7—partial peptide sequence obtained from isolated hydantoinase Abbreviations:
NCBPA—N-carbamoyl-β-phenylalanine
6PDHU—6-phenyldihydrouracil

The invention claimed is:

1. A process for the biocatalytic production of a β-amino acid precursor, comprising:
reacting at least one substrate of the general formula (I)

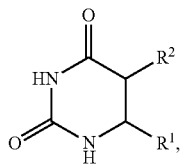

(I)

wherein R¹ and R² independently from each other are selected from:
hydrogen;
a linear or branched, optionally substituted, lower alkyl group;
a linear or branched, optionally substituted, lower alkenyl group;
an optionally substituted cyclic alkyl group;
a mono- or polycyclic, optionally substituted aryl group;
a mono- or polycyclic, optionally substituted heteroaryl group;
a linear or branched, optionally substituted alkoxy group;
an amino group;
a linear or branched, optionally substituted alkylamino group;
a linear or branched, optionally substituted alkylthio group;
a linear or branched, optionally substituted acyl group,
a carboxyl group or
an aldehyde group;
said substrate being present in stereoisomerically pure form or as a mixture of stereoisomers, wherein the stereoisomerically pure form or the mixture of stereoisomers may optionally be a salt,
in the presence of at least one enzyme, catalyzing the hydrolytic cleavage of a hydantoin and/or dihydropyrimidin ring,
so that a β-amino acid precursor of the general formula (II)

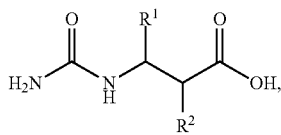

(II)

wherein R¹ and R² are identified as above,
is produced;
said process being characterized in that the at least one enzyme which is applied in said process is
a) an enzyme having hydantoinase and/or dihyropyrimidinase activity which is obtained from *Vigna angularis* and comprising at least one of the amino acid sequences of SEQ ID NO: 5 and SEQ ID NO: 7;
or
b) an enzyme having 1 to 20 amino acid additions, substitutions, deletions and/or inversions relative to the enzyme of a), wherein said enzyme comprises an amino acid sequence having at least 95% sequence identity to SEQ ID NO: 5 or SEQ ID NO 7, and has hydantoinase and/or dihydropyrimidinase activity.

2. The process according to claim 1, furthermore comprising converting said β-amino acid precursor of formula (II) to the corresponding β-amino acid of the formula (III)

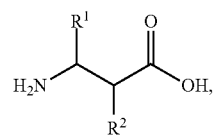

(III)

wherein R¹ and R² have the same meaning as defined in claim 1.

3. The process according to claim 2, wherein the conversion of the β-amino acid precursor is takes place at an acidic pH or in the presence of a carbamoylase.

4. The process according to claim 1, wherein R¹ is H and R2 is an optionally substituted aryl group.

5. The process according to claim 1, wherein the reaction is performed in a Tris-buffered or a borate-buffered reaction mixture.

6. The process according to claim 1, wherein the reaction is performed at a pH from about 7.0 to about 11.0.

7. The process according to claim 1, wherein the reaction is performed in the presence of approximately 1% to approximately 20% dimethylsulfoxide.

8. The process according to claim 1, wherein the reaction is performed at a temperature in the range of about 30° C. to about 60° C.

9. The process according to claim 1, wherein the reaction is performed from about 1 hour to about 25 hours.

10. The process according to claim 1, wherein the at least one substrate is a dihydrouracil which is monosubstituted at the 5-position or at the 6-position.

11. The process of claim 1, wherein the at least one enzyme comprises the amino acid sequence of SEQ ID NO: 5 and the amino acid sequence of SEQ ID NO: 7.

12. The process of claim 1, wherein the reaction is performed in a Tris-buffered reaction mixture.

13. The process of claim 1, wherein the reaction is performed at a pH from about 7.5 to about 8.0.

14. The process of claim 1, wherein the reaction is performed in the presence of approximately 10% dimethylsulfoxide.

15. The process of claim 1, wherein the reaction is performed at a temperature in the range of about 40° C. to about 50° C.

16. The process of claim 1, wherein the reaction is performed from about 4 hours to about 5 hours.

17. The process of claim 1, wherein the at least one substrate is selected from the group consisting of 6-phenyldihydrouracil, 4-fluoro-6-phenyldihydrouracil, 3-bromo-6-phenyldihydrouracil, 5-methyldihydrouracil, and 6-methyldihydrouracil.

18. The process of claim 1, wherein the at least one enzyme has a molecular weight of about 55 kD.

* * * * *